US007445892B2

(12) United States Patent
Owa et al.

(10) Patent No.: US 7,445,892 B2
(45) Date of Patent: Nov. 4, 2008

(54) METHOD OF TESTING ANTICANCER AGENT-SENSITIVITY OF TUMOR CELLS

(75) Inventors: Takashi Owa, Tsukuba (JP); Akira Yokoi, Tsukuba (JP); Junro Kuromitsu, Ibaraki (JP); Takatoshi Kawai, Tsukuba (JP); Hiroyuki Kato, Ibaraki (JP); Takeshi Nagasu, Tsuchiura (JP)

(73) Assignee: Eisai Co., Ltd., Bunkyo-Ku, Tokyo (JP)

( * ) Notice: Subject to any disclaimer, the term of this patent is extended or adjusted under 35 U.S.C. 154(b) by 317 days.

(21) Appl. No.: 10/432,661

(22) PCT Filed: Nov. 26, 2001

(86) PCT No.: PCT/JP01/10282

§ 371 (c)(1),
(2), (4) Date: May 23, 2003

(87) PCT Pub. No.: WO02/42493

PCT Pub. Date: May 30, 2002

(65) Prior Publication Data

US 2004/0115664 A1    Jun. 17, 2004

(30) Foreign Application Priority Data

Nov. 24, 2000    (JP)    ............... 2000-357398

(51) Int. Cl.
*C12Q 1/68*    (2006.01)
(52) U.S. Cl. .......................................................... 435/6
(58) Field of Classification Search .................. 435/6, 435/4
See application file for complete search history.

(56) References Cited

FOREIGN PATENT DOCUMENTS

| WO | WO 95/07276 | 3/1995 |
|---|---|---|
| WO | WO0055320 A1 * | 9/2000 |
| WO | WO 2006/036025 A1 | 4/2006 |

OTHER PUBLICATIONS

Staunton et al. (PNAS 2001; 98: 10787-10792).*
Perou et al. (PNAS 1999; 96: 9212-9217).*
Alizadeh et al. (Nature 2000; 403: 503-511).*
Yokoi et al. (Molecular Cancer Therapeutics 2002; 1: 275-286).*
Owa et al. (Bioorg. Med. Chem. Lett. 2000; 10: 1223-1226).*
Stanislas et al. (Biochemical and Biophysical Research Communications 1998; 157: 1309-1315).*
Kudoh, et al., "Monitoring the Expression Profiles of Doxorubicin-Induced and Doxorubicin-Resistant Cancer Cells by cDNA Microarry", *Cancer Research*, 60: 4161-4166, 2000.
Rhee, et al., "Characterization of Cellular Pathways Involved in Glioblastomas Response to Chemotherapeutic Agent 1, 3-Bis(2-Chloroethyl)-1-Nitrosourea (BCNU) by Gene Expression Profiling", *Oncology Reports*, 6: 393-401, 1999.
Owa, et al. "Discovery of Novel Antitumor Sulfonamides Targeting G1 Phase of the Cell Cycle," *Journal of Medical Chemistry*, vol. 42, No. 19, pp. 3789-3799, 1999.
Owa, et al. "A Focused Compound Library of Novel *N*-(7-Indolyl)benzenesulfonamides for the Discovery of Potent Cell Cycle Inhibitors," *Bioorganic & Medicinal Chemistry Letters*, vol. 10, No. 11, pp. 1223-1226, 2000.
Ozawa, et al. "E7070, A Novel Sulphonamide Agent with Potent Antitumor Activity in Vitro and In Vivo," *European Journal of Cancer*, vol. 37, No. 17, pp. 2275-2282, 2001.
Owa, et al., "Microarry-based Expression Profiling Of Sulfonamide Anti-tumor Agents," *Proceedings of the American Association for Cancer Research Annual Meeting*, 42: 371, 2001.
Watanabe, et al., "A Novel Anti-tumor Agent ER-35744, Targeting G1 Phase. III: Studies Of Mechanism Of Action," *Proceedings of the American Association for Cancer Research Annual Meeting*, 37: 391, 1996.
Wu, et al., "Multidrug-Resistant Phenotype Of Disease-oriented Panels Of Human Tumor Cell Lines Used For Anti-cancer Drug Screening," *Cancer Research*, 52: 3029-3034, 1992.
Supplementary European Search Report EP 01997200.9—2405 PCT/JP0110282, Dated Jan. 27, 2006, 2 pgs.
Scherf, et al., *Nature Genetics*, 24(3): 236-244, Mar. 2000.
Zimmermann, et al., *Oncogene*, 19(25): 2913-2920, Jun. 8, 2000.

* cited by examiner

*Primary Examiner*—Brandon J Fetterolf
(74) *Attorney, Agent, or Firm*—Choate Hall & Stewart LLP; C. Hunter Baker (57) ABSTRACT

Susceptibility of a tumor cell to an anticancer agent is tested by measuring an expression level or levels of a gene or genes selected from the group consisting of the genes listed in Tables 3 and 4 in a tumor cell collected from a cancer patient treated with an anticancer agent (E7070 and related compounds thereof), or causing the anticancer agent to act on a tumor cell collected from a cancer patient and measuring an expression level or levels of a gene or genes selected from the group consisting of the genes listed in Tables 3 and 4 in the tumor cell, and determining that the tumor cell is susceptible to the anticancer agent when the expression level or levels of the gene or genes listed in Table 3 increase, or the expression level or levels of the gene or genes listed in Table 4 decrease.

8 Claims, 3 Drawing Sheets

METHOD OF TESTING ANTICANCER AGENT-SENSITIVITY OF TUMOR CELLS

This is the U.S. National Phase under 35 U.S.C. § 371 of International Application PCT/JP01/10282, filed Nov. 26, 2001, which was published in a language other than English which claims priority of JP 2000-357398, filed Nov. 24, 2000. Each of the above applications are incorporated herein by reference in their entirety.

TECHNICAL FIELD

The present invention relates to a method for testing whether a tumor cell is susceptible to an anticancer agent or not.

BACKGROUND ART

In a conventional clinical study of an anticancer agent, its toxicity profile and maximum recommended dose are first determined in the Phase I clinical study, and then the agent is evaluated as a drug based on the response rate using the tumor reduction rate as a criterion for efficacy in the Phase II clinical study. Meanwhile, with the advancement in cancer biology in recent years, drugs having a novel action mechanism for inhibiting the intracellular signal transduction system, angiogenesis and so forth are in the course of active research and development. For these novel anticancer agents, it may be possible that a maximum recommended dose close to a toxic dose does not necessarily need to be administered. Further, it is estimated that drug efficacy could be more appropriately judged by using improvement of QOL (Quality of Life) or prolongation of life associated with tumor growth inhibition as an index rather than tumor reduction. In this case, to more logically and specifically confirm the drug efficacy, it is desirable to utilize change of a biological marker closely relating to a tumor growth inhibition mechanism as a surrogate marker.

In the anticancer therapy, in general, reactivity of a living body when an anticancer agent is administered is largely depends on susceptibility of a tumor cell, which is a target of the drug, to the drug. Generally, this susceptibility of tumor cell to the drug greatly varies in every type of tumor cell. Such differences in susceptibility are attributable to quantitative or qualitative differences of target molecules of the drug or factors relating to the molecules, acquisition of drug resistance and so forth. Considering such a background, it would be very useful if change in a tumor cell specifically caused when the tumor cell as a target exhibits susceptibility to a drug can be measured by using tumor tissue obtained by biopsy etc., because early determination of drug efficacy, establishment of a treatment method, selection of a new treatment method and so forth become possible by using the change as a surrogate marker. Further, if a tumor cell is isolated from tumor tissue obtained by biopsy or the like in a conventional manner prior to a treatment and then treated with a drug, and whether this tumor cell is susceptible to the drug is determined based on change of the aforementioned surrogate marker, it becomes possible to preliminarily predict whether the treatment using the drug is effective or not, and this would be extremely useful in clinical practice. It is important that the change of this surrogate marker should be specific to antitumor effect, and it is sufficient that the change can be measured with high sensitivity. Specifically, quantification of variations in the gene expression specific to the antitumor effect of the drug, analysis of quantitative variations of a protein along with the changes in gene expression, analysis of functional changes associated with these changes and so forth can be used as the surrogate markers.

E7070 (N-(3-chloro-7-indolyl)-1,4-benzenedisulfonamide) is a compound that has an antitumor effect targeting the G1 phase of the cell cycle, and is being clinically developed (Takashi Owa, Hiroshi Yoshino, Tatsuo Okauchi, Kentaro Yoshimatsu, Yoichi Ozawa, Naoko Hata Sugi, Takeshi Nagasu, Nozomu Koyanagi and Kyosuke Kitoh, J. Med. Chem, 1999, 42, 3789-3799).

Spectra of intensity of the growth inhibitory action of this compound on various tumor cells are different from those of any of existing anticancer agents, and this compound is expected to have an effect as an anticancer agent having a novel action mechanism. In order to accelerate the clinical development of this drug and early establish a clinical treatment method, and contribute to improvement of QOL of patients by efficiently advancing treatment based on established treatment methods, it is desirable to discover and apply a surrogate marker that can be specifically used upon the administration of the drug.

In recent years, methods of using various DNA microarrays to detect expression levels of a large number of genes at the same time have been established and widely used (Schena M, Shalon D, Davis R W, Brown P O, Science 1995, 270, 467-70; Lockhart, D. J., Dong, H., Byrne, M. C., Follettie, M. T., Gallo, M. V., Chee, M. S., Mittmann, M., Wang C., Kobayashi, M., Horton, H. Brown, E. L., Nature Biotechnology, 1996, 14, 1675-1680).

Also in the field of cancer studies, researches using such DNA microarrays are actively being conducted. For example, in a study in which diffuse large B-cell lymphoma (DLBCL) was investigated by expression analysis using a DNA microarray, DLBCL has been classified into two of different types according to differences in gene expression profiles, and it has been shown that this classification leads to prediction of prognosis (Alizadeh A A, Eisen M B, Davis R E, Ma C, Lossos I S, Rosenwald A, Boldrick J C, Sabet H, Tran T, Yu X, Powell J I, Yang L, Marti G E, Moore T, Hudson J Jr, Lu L, Lewis D B, Tibshirani R, Sherlock G, Chan W C, Greiner T C, Weisenburger D D, Armitage J O, Warnke R, Staudt L M, et al, Nature, 2000, 403, 503-11). Further, there have been a report in which, by analyzing gene expression profiles of a panel of 60 types of cancer cell lines from the National Cancer Institute in the United States, these cell lines were reclassified and their characteristics were examined (Ross D T, Scherf U, Eisen M B, Perou C M, Rees C, Spellman P, Iyer V, Jeffrey S S, Van de Rijn M, Waltham M, Pergamenschikov A, Lee J C, Lashkari D, Shalon D, Myers T G, Weinstein J N, Botstein D, Brown P O, Nat Genet, 2000, 24, 227-35), a report in which relationships of the gene expression profiles of the panel of 60 types of cancer cell lines and susceptibility to various anticancer agents of each cell line were discussed (Scherf U, Ross D T, Waltham M, Smith L H, Lee J K, Tanabe L, Kohn K W, Reinhold W C, Myers T G, Andrews D T, Scudiero D A, Eisen M B, Sausville E A, Pommier Y, Botstein D, Brown P O, Weinstein J N, Nat Genet, 2000, 24, 236-44) and so forth.

Further, there have also been several reports in which changes in gene expression that occurred when anticancer agents were caused to act on tumor cells were examined by similarly using a DNA microarray (partly macroarray using a membrane filter) (Rhee C H, Ruan S, Chen S, Chenchik A, Levin V A, Yung A W, Fuller G N, Zhang W, Oncol Rep, 1999, 6, 393-401. Zimmermann J, Erdmann D, Lalande I, Grossenbacher R, Noorani M, Furst P, Oncogene, 2000, 19, 2913-20. Kudoh K, Ramanna M, Ravatn R, Elkahloun A G, Bittner M L, Meltzer P S, Trent J M, Dalton W S, Chin K V, Cancer Res, 2000, 4161-6). These reports show that the analysis of variations in gene expression is extremely useful in comparison of characteristics of two or more cell populations and comprehensive studies of biological changes of cells caused by drug treatment or the like at a molecular level.

DISCLOSURE OF THE INVENTION

An object of the present invention is to provide surrogate markers for antitumor effect of E7070 and its related compounds in cases that the compounds are caused to act on tumor cells.

The inventors of the present invention analyzed changes in gene expression caused when E7070 and its related compounds were caused to act on tumor cells susceptible to these anticancer agents by the DNA microarray method and found changes in gene expression caused by these anticancer agents in common.

Further, they also found that, among these genes, there were genes that exhibited changes of expression common to three kinds of cancers and that expression changes of these genes can be used as surrogate markers for the antitumor effect of E7070 and its related compounds, and thus accomplished the present invention.

The present invention provides the followings.

1. A method for testing susceptibility of a tumor cell to an anticancer agent, which comprises:

1) measuring an expression level or levels of a gene or genes selected from the group consisting of the genes listed in Tables 3 and 4 in a tumor cell collected from a cancer patient treated with an anticancer agent represented by the following general formula (I):

(I)

wherein A represents a monocyclic or bicyclic aromatic ring, which may be substituted, B represents a 6-membered unsaturated hydrocarbon ring or a 6-membered unsaturated heterocyclic ring containing one nitrogen atom as a heteroatom, each of which may be substituted, C represents a 5-membered heterocyclic ring containing one or two nitrogen atoms, which may be substituted, W represents a single bond or —CH=CH—, X represents —N($R^1$)— or an oxygen atom, Y represents a carbon or nitrogen atom,

Z represents —N($R^2$)— or a nitrogen atom, and $R^1$ and $R^2$ may be identical or different and each represent a hydrogen atom or a lower alkyl group, and 2) determining that the tumor cell is susceptible to the anticancer agent when the expression level or levels of the gene or genes listed in Table 3 increase, or the expression level or levels of the gene or genes listed in Table 4 decrease in comparison with those in a tumor cell collected from the cancer patient before the treatment with the anticancer agent.

2. A method for testing susceptibility of a tumor cell to an anticancer agent, which comprises:

1) causing an anticancer agent to act on a tumor cell collected from a cancer patient, the said anticancer agent being represented by the following general formula (I):

(I)

wherein A represents a monocyclic or bicyclic aromatic ring, which may be substituted, B represents a 6-membered unsaturated hydrocarbon ring or a 6-membered unsaturated heterocyclic ring containing one nitrogen atom as a heteroatom, each of which may be substituted, C represents a 5-membered heterocyclic ring containing one or two nitrogen atoms, which may be substituted, W represents a single bond or —CH=CH—, X represents —N($R^1$)— or an oxygen atom, Y represents a carbon or nitrogen atom, Z represents —N($R^2$)— or a nitrogen atom, and $R^1$ and $R^2$ may be identical or different and each represent a hydrogen atom or a lower alkyl group, 2) measuring an expression level or levels of a gene or genes selected from the group consisting of the genes listed in Tables 3 and 4 in the tumor cell, and 3) determining that the tumor cell is susceptible to the anticancer agent when the expression level or levels of the gene or genes listed in Table 3 increase, or the expression level or levels of the gene or genes listed in Table 4 decrease in comparison with those in an untreated tumor cell.

3. The method according to 1 or 2, wherein the expression level or levels of the gene or genes are measured by quantifying an RNA or RNAs which are a transcription product or products of the gene or genes by using a DNA microarray.

4. The method according to 1 or 2, wherein the expression level or levels of the gene or genes are measured by quantifying an RNA or RNAs which are a transcription product or products of the gene or genes by quantitative PCR.

5. A reagent for quantifying an RNA for use in the method as defined in 4, which comprises an oligonucleotide complementary to the RNA as a component.

6. The method according to 1 or 2, wherein the expression level or levels of the gene or genes are measured by quantifying a protein or proteins which are a gene product products of the gene or genes by an immunochemical method.

7. The method according to 6, wherein the expression level or levels of the gene or genes are measured by quantifying a protein or proteins which are a gene product or products of the gene or genes by ELISA.

8. The method according to 6, wherein the expression level or levels of the gene or genes are measured by quantifying a protein or proteins which are a gene product or products of the gene or genes by Western blotting.

9. An immunoassay reagent used in the method as defined in 6, which comprises an antibody directed to the protein as a component.

10. The method according to 1 or 2, wherein A represents benzene or pyridine which may be substituted, B represents benzene which may be substituted, C represents pyrrole

BEST MODE FOR CARRYING OUT THE INVENTION

Hereafter, embodiments of the present invention will be described in detail.

The test method of the present invention is characterized in that a change in expression level of a gene in a tumor cell caused when the tumor cell is exposed to an anticancer agent in vivo or in vitro is used as an index of susceptibility of the tumor cell to the anticancer agent.

Therefore, the test method of the first embodiment of the present invention comprises the steps of 1) measuring an expression level or levels of a gene or genes selected from the group consisting of the genes listed in Tables 3 and 4 of a tumor cell collected from a cancer patient treated with an anticancer agent represented by the general formula (I), and 2) determining that the tumor cell is susceptible to the anticancer agent when the expression level or levels of the gene or genes listed in Table 3 increase, or the expression level or levels of the gene or genes listed in Table 4 decrease in comparison with those in a tumor cell collected from the cancer patient before the treatment with the anticancer agent.

Further, the test method of the second embodiment of the present invention comprises the steps of 1) causing an anticancer agent represented by the general formula (I) to act on a tumor cell collected from a cancer patient, 2) measuring an expression level or levels of a gene or genes selected from the group consisting of the genes listed in Tables 3 and 4 in the tumor cell, and 3) determining that the tumor cell is susceptible to the anticancer agent when the expression level or levels of the gene or genes listed in Table 3 increase, or the expression level or levels of the gene or genes listed in Table 4 decrease in comparison with those in an untreated tumor cell.

The anticancer agent used in the present invention is a sulfonamide derivative or a sulfonnic acid ester derivative represented by the general formula (I).

In the general formula (I), the "monocyclic or bicyclic aromatic ring, which may be substituted" represented by A is an aromatic hydrocarbon ring or an aromatic heterocyclic ring containing at least one of nitrogen, oxygen and sulfur atoms, each of which may have one to three substituents thereon. Examples of such aromatic rings included in the ring A include pyrrole, pyrazole, imidazole, thiophene, furan, thiazole, oxazole, benzene, pyridine, pyrimidine, pyrazine, pyridazine, naphthalene, quinoline, isoquinoline, phthalazine, naphthyridine, quinoxaline, quinazoline, cinnoline, indole, isoindole, indolizine, indazole, benzofuran, benzothiophene, benzoxazole, benzimidazole, benzopyrazole, benzothiazole and so forth. They may have one to three substituents. When two or more substituents are present, they may be the same or different. Examples of the substituents include an amino group which may be substituted with a lower alkyl or lower cycloalkyl group, a lower alkyl group, a lower alkoxy group, hydroxyl, nitro, mercapto, cyano, a lower alkylthio group, halogen, a group represented by the formula -a-b [wherein a represents a single bond, —$(CH_2)_k$—, —O—$(CH_2)_k$—, —S—$(CH_2)_k$— or —N($R^3$)—$(CH_2)_k$— (k is an integer of 1 to 5, $R^3$ represents a hydrogen atom or a lower alkyl group), and b represents —$CH_2$-d (wherein d represents an amino group which may be substituted with a lower alkyl group, halogen, hydroxyl, a lower alkylthio group, cyano or a lower alkoxy group)], a group represented by the formula -a-e-f [wherein a has the same meaning as defined above, e represents —S(O)— or —$S(O)_2$—, f represents an amino group which may be substituted with a lower alkyl or lower alkoxy group, a lower alkyl group, trifluoromethyl, —$(CH_2)_m$-b or —N($R^4$)—$(CH_2)_m$-b (wherein b has the same meaning as defined above, $R^4$ represents a hydrogen atom or a lower alkyl group, and m is an integer of 1 to 5)], a group represented by the formula -a-g-h [wherein a has the same meaning as defined above, g represents —C(O)— or —C(S)—, h represents an amino group which may be substituted with a lower alkyl group, hydroxyl, a lower alkyl group, a lower alkoxy group, —$(CH_2)_n$-b or —N($R^5$)—$(CH_2)_n$-b (wherein b has the same meaning as defined above, $R^5$ represents a hydrogen atom or a lower alkyl group, and n is an integer of 1 to 5)], a group represented by the formula -a-N($R^6$)-g-i [wherein a and g have the same meanings as defined above, $R^6$ represents a hydrogen atom or a lower alkyl group, i represents a hydrogen atom or a lower alkoxy group or f (f has the same meaning as defined above)], a group represented by the formula -a-N($R^7$)-e-f (wherein a, e and f have the same meanings as defined above, and $R^7$ represents a hydrogen atom or a lower alkyl group) and group represented by the formula —$(CH_2)_p$-j-$(CH_2)_q$-b (wherein j represents an oxygen or sulfur atom, b has the same meaning as defined above, and p and q may be the same or different and each represent an integer of 1 to 5) and so forth.

When the substituent is an amino group substituted with two of alkyl groups, both of the alkyl groups may bond to form a 5- or 6-membered ring. Further, when A is a nitrogen-containing heterocyclic ring having hydroxyl or mercapto, these groups may present in the form of an oxo or thioxo group by resonance.

The "6-membered unsaturated hydrocarbon ring or 6-membered unsaturated heterocyclic ring containing one nitrogen atom as a heteroatom, which may be substituted" represented by B means benzene or pyridine which may be partially hydrogenated. It may have one or two of substituents on the ring, and when two of substituents are present, they may be the same or different.

The "5-membered heterocyclic ring containing one or two nitrogen atoms, which may be substituted" represented by C means pyrrole, pyrazole or imidazole which may be partially hydrogenated. It may have one or two of substituents on the ring, and when two of substituents are present, they may be the same or different.

Examples of the substituents that the rings of B and C may have include halogen, cyano, a lower alkyl group, a lower alkoxy group, hydroxyl, oxo, a group represented by the formula —C(O)-r (wherein r represents a hydrogen atom, an amino group which may be substituted with a lower alkyl group, a lower alkyl group, a lower alkoxy group or hydroxyl), an amino group substituted with a lower alkyl group, trifluoromethyl and so forth.

In the general formula (I), the lower alkyl group in the definitions of $R^1$ and $R^2$ as well as the substituents that the rings of A, B and C may have means a linear or branched alkyl group having 1 to 6 carbon atoms, and examples thereof include methyl, ethyl, n-propyl, isopropyl, n-butyl, isobutyl, sec-butyl, tert-butyl, n-pentyl (amyl), isopentyl, neopentyl, tert-pentyl, 1-methylbutyl, 2-methylbutyl, 1,2-dimethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl and so forth. Among these, methyl, ethyl, n-propyl, isopropyl, n-butyl and isobutyl are preferred, and methyl, ethyl, n-propyl and isopropyl are most preferred.

The lower cycloalkyl group mentioned in the definitions of the substituents that the ring of A may have means a cycloalkyl group having 3 to 8 carbon atoms, and examples thereof include cyclopropyl, cyclopentyl, cyclohexyl and so forth.

The lower alkoxy mentioned in the definitions of the substituents that the rings of A, B and C may have means an alkoxyl group derived from the aforementioned lower alkyl group, such as methoxy, ethoxy, n-propoxy, isopropoxy, n-butoxy, isobutoxy and tert-butoxy. Among these, methoxy and ethoxy are most preferred. The lower alkylthio group means an alkylthio group derived from the aforementioned lower alkyl group. Further, examples of the halogen include fluorine, chlorine, bromine and so forth.

The sulfonamide derivatives or sulfonic acid ester derivatives represented by the general formula (I) may form a salt with an acid or a base. The anticancer agent used in the present invention also includes salts of the compounds represented by the general formula (I). Examples of the salt with an acid include salts with inorganic acids, such as hydrochlorides, hydrobromides and sulfates, and salts with organic acids such as acetic acid, lactic acid, succinic acid, fumaric acid, maleic acid, citric acid, benzoic acid, methanesulfonic acid and p-toluenesulfonic acid, and examples of the salt with a base include salts with inorganic bases, such as sodium salts, potassium salts and calcium salts and salts with organic bases such as triethylamine, arginine and lysine.

It is needless to say that the compounds include hydrates and optical isomers of these compounds if they are present. The anticancer agent used in the present invention exhibits a high antitumor activity, and the anticancer agents also includes compounds which undergo metabolism such as oxidation, reduction, hydrolysis and conjugation in vivo to exhibit the antitumor activity. Further, the anticancer agent used in the present invention includes compounds which undergo metabolism in vivo such as oxidation, reduction and hydrolysis to form compounds represented by the general formula (I).

Tumor cells of which susceptibility is tested are not particularly limited so long as they are susceptible to the anticancer agent represented by the general formula (I). Examples thereof include tumor cells derived from colon cancer, lung cancer, breast cancer, leukemia, pancreas cancer, kidney cancer, melanoma, malignant lymphoma, head and neck cancer, gastric cancer and so forth.

The tumor cells collected from a cancer patient include tumor cells contained in a cancer tissue isolated from the cancer patient.

In the test method of the first embodiment, the tumor cell collected from a cancer patient may be a tumor cell collected from a cancer patient treated with an anticancer agent represented by the general formula (I) in such an amount that susceptibility of the tumor cell can be measured. Usually, tumor cells collected from a cancer patient treated with a dose of 100 to 1500 mg for 1 to 14 days are used.

In the test method of the second embodiment, conditions for causing the anticancer agent represented by the general formula (I) to act on a tumor cell collected from a cancer patient are not limited so long as susceptibility of the tumor cells can be measured, and culture is usually performed in a medium containing the anticancer agent at a concentration of 0.01 to 10 µM for 6 to 72 hours.

The gene expression level can be measured by quantifying RNA as a gene transcription product or a protein as a gene product. The RNA or protein can be quantified usually by extracting the RNA or protein from tumor cells and quantifying the RNA or protein in the extract. Hereafter, examples of 1. extraction of RNA or protein, 2. quantification of RNA, and 3. quantification of protein will be explained in detail in this order.

1. Extraction of RNA or Protien

1) Extraction of RNA or protein from cancer tissue of patient treated with anticancer agent represented by general formula (I)

RNA or protein is extracted from a cancer tissue collected by biopsy or the like from a patient treated with an anticancer agent represented by the general formula (I) by the method described below.

RNA can be extracted according to a usual RNA extraction method. For example, extraction can be carried out by using TRIZOL Reagent (Life Technologies Oriental) or the like according to the attached operation manual. Specifically, a cancer tissue with 1 ml of TRIZOL reagent per 50 to 100 mg of the cancer tissue is homogenized by using a Teflon homogenizer. The mixture is centrifuged (12,000×g, 10 minutes, 4° C.), and the obtained supernatant is left at room temperature for 5 minutes and 0.2 ml of chloroform is added thereto per 1 ml of the used TRIZOL Reagent. The resulting solution is vigorously stirred by shaking for 15 seconds, left at room temperature for 2 to 3 minutes and then centrifuged (12,000× g, 15 minutes, 4° C.). After the centrifugation, the aqueous layer is transferred to a new tube, and 0.5 ml of isopropyl alcohol is added per 1 ml of the used TRIZOL reagent. The mixture is left at room temperature for 10 minutes and centrifuged (12,000×g, 10 minutes, 4° C.). The obtained precipitates are washed with 75% ethanol, air-died and used in subsequent operations as total RNA.

Protein can be extracted from a cancer tissue according to the methods described in Bollag, D. M., Rozycki M. D., Edelstein S. J., Protein Methods, 1996, Wiley-Liss, Inc., New York, U.S.A.; Walker, J. M., The protein handbook, 1996, Humana Press, New Jersey, U.S.A. and so forth.

2) Extraction of RNA or protein from cancer cell cultured in the presence of anticancer agent represented by general formula (I)

Cancer cells (tumor cells) are isolated in a conventional manner from a cancer tissue obtained from a patient by biopsy or the like. For example, according to the method of Hamburger et al. (Hamburger A., Salmon S. E., Kim M. B., Trent J. M., Soehnlen B. J., Alberts D. S. and Schmidt H. T., Cancer Res., 38, 3438-3443, 1978), the obtained tissue is aseptically chopped, and then a cell suspension is prepared by using a stainless mesh, injection needle, nylon mesh or the like. The obtained cells are cultured in a suitable medium (for example, RPMI-1640, MEM, McCoy medium etc. containing 10-15% FCS). The obtained cancer cells are cultured at 37° C. in the presence of the anticancer agent represented by the general formula (I) under 5% $CO_2$ condition for a suitable period, preferably, for 3, 6, 12 or 24 hours, more preferably for 12 hours, and RNA or protein is extracted by the method described below. Further, it is also possible to specifically isolate only cancer cells from a tissue obtained by biopsy or the like by using the soft agar culture method (Hamburger A., and Salmon S. E., Science, 197, 461-463, 1977; Hamburger A., and Salmon S. E., J. Clin. Invest., 60, 846-854, 1977; Von Hoff D. D., and Johnson, G. E., Proc. Am. Assoc. Cancer Res., 20, 51, 1979) and use them.

RNA can be extracted from a cancer cell according to a usual RNA extraction method as the extraction of RNA from a cancer tissue. For example, when TRIZOL Reagent (Life Technologies Oriental) is used, extraction can be carried out according to the attached operation manual. Specifically, 1 ml of TRIZOL Reagent is added per 5 to $10 \times 10^6$ cancer cells, and the same operations as in the extraction of RNA from a cancer tissue can be performed.

Extraction of protein from cancer cells can also be carried out according to methods described in publications as in the extraction from cancer tissue.

2. Quantification of RNA

RNA can be quantified by techniques of Northern blotting analysis, DNA microarray analysis, RT-PCR, quantitative PCR and so forth. It is preferable to use a DNA microarray or quantitative PCR. These techniques will be explained below, but the present invention is not limited to them.

Quantification by using a DNA microarray is performed as follows. First, double-stranded cDNA is synthesized by using the obtained RNA as a template, SuperScript Choice System (Life Technologies Oriental) and $T7-d(T)_{24}$ primer. Subsequently, biotinylated cRNA is synthesized by using the cDNA as a template.

Specifically, single-stranded DNA is first synthesized from the obtained RNA by using the $T7-d(T)_{24}$ primer. Then, dNTP, DNA ligase, DNA polymerase I and RNase H are added thereto to react them and T4 DNA polymerase I is further added thereto to complete the synthesis of double-stranded cDNA. The obtained cDNA is purified, and then biotinylated UTP and CTP are added to allow a labeling reaction by using RNA Transcript Labeling Kit (Enzo Diagnostics). The reaction product is purified and heated at 94° C. in 200 mM Tris/acetate (pH 8.1), 150 mM magnesium acetate, 50 mM potassium acetate for 35 minutes to obtain fragmented cRNA.

The fragmented cRNA is hybridized with GeneChip Hu6800 (Affymetrix) or an update product, for example, in 100 mM MES, 1 M sodium salt, 20 mM EDTA, 0.01% Tween 20 at 45° C. for 16 hours. After the hybridization, the GeneChip is washed and stained according to the protocol EukGE-WS2 attached to the Affymetrix Fluidics Station. For the staining, streptavidin-phycoerythrin and biotinylated goat anti-streptavidin antibody are used. The stained GeneChip is scanned by using HP Argon Ion Laser Confocal Microscope (Hewlett Packard) to measure its fluorescence intensity. When this fluorochrome is used, fluorescence is measured at 570 nm by using an excitation light at 488 nm.

The quantitative data analysis is preferably conducted by using GeneChip Software (Affymetrix). To quantify RNA, an average of "differences [(Perfect match hybridization signal)−(Mismatch signal)]" is obtained for each probe family. When this value is 50 or higher, and quantitative values of RNA obtained under two kinds of conditions diverge, preferably when they diverge 1.8 times or more, it is determined that the gene expression has significantly "increased" or "decreased".

When the RNA level or levels of the gene or genes listed in Table 3 increase, or the RNA level or levels of the gene or genes listed in Table 4 decrease, it is determined that the tumor cells are susceptible to the anticancer agent.

Further, quantitative PCR is performed as follows by using SYBR Green and ABI Prism 7700 Sequence Detection System (Perkin-Elmer Applied Biosystems).

The operation is performed in two steps of a reverse transcription reaction and PCR reaction. The reverse transcription reaction as the first step is carried out by adding dNTP, oligo $d(T)_{16}$ primer, RNase inhibitor mixture and Multiscribe Reverse Transcriptase (Perkin-Elmer Applied Biosystems) to the obtained RNA, keeping the mixture at 25° C. for 10 minutes and then heating the mixture at 48° C. for 30 minutes. The reaction is terminated by heating at 95° C. for 5 minutes.

The obtained cDNA is subjected to the PCR reaction as the second step. The PCR reaction is carried out, for example, in a reaction system composed of 4 ng of cDNA, 1×SYBR PCR buffer, 3 mM $MgCl_2$, 200 μM each of dATP, dCTP and dGTP, 400 μM dUTP, 200 nM primer pair, 0.01 U/μl AmpErase UNG and 0.025 U/μl AmpliTaq Gold DNA Polymerase (Perkin-Elmer Applied Biosystems). The PCR reaction is performed with, for example, reactions at 50° C. for 2 minutes and at 95° C. for 10 minutes followed by a cycle of reactions at 95° C. for 20 seconds, at 55° C. for 20 seconds and at 72° C. for 30 seconds, which are repeated 40 times. The primers and the probe are designed, for example, by using Primer Expression (Perkin-Elmer Applied Biosystems). For comparison of two or more specimens, a quantified value is corrected into transcription amount in each specimen by using mRNA level of a house keeping gene, which shows little variation in transcription amount, preferably mRNA level of GAPDH, and used.

When the RNA level or levels of the gene or genes listed in Table 3 increase, or the RNA level or levels of the gene or genes listed in Table 4 decrease, it is determined that the tumor cells are susceptible to the anticancer agent.

The present invention also provides a reagent for quantifying RNA for use in the test method of the present invention, which comprises an oligonucleotide complementary to RNA as a transcription product of a gene of which expression level is to be measured, as a component. The oligonucleotide included as a component is a primer and/or probe used in quantitative PCR and can be designed as described above. The RNA-quantifying reagent of the present invention may contain components conventionally used in an ordinary quantifying reagent in addition to the above oligonucleotide.

3. Quantification of Protein

Although protein is quantified based on its activity or antigenicity, quantification based on antigenicity, i.e., immunochemical quantification, which can be easily and generally applied to proteins, is preferred.

As for antibody directed to a protein, an antigen determinant is predicted from the amino acid sequence based on the report of Parker et al. (Parker J. M. R., Guo D., Hodges R. S., Biochemistry, 25, 5425, 1986) or the report of Karplus et al. (Karplus P. A., Schulz G. E., Naturwissenschaften, 72, 212, 1985) to synthesize a peptide. Alternatively, a fusion protein, for example, a fusion protein with glutathione synthetase (GST) is expressed and purified by using a glutathione column to produce an antigen, and a rabbit, a mouse or the like is immunized with the obtained antigen to produce polyclonal or preferably monoclonal antibodies (Harlow E., Lane D., Antibodies: A Laboratory Manual, 1988, Cold Spring Harbor Laboratory Press, New York). Further, when commercially available antibodies are available, they can also be used after their specificity is confirmed.

By using the obtained antibodies, ELISA or RIA is performed to quantify the protein, for example, by the enzyme immunoassay method (Ishikawa E. et al., Igakushoin, 1982) or the method described in Ishikawa E., Kawai T., Miyai, K., Enzyme Immunoassay, Igakushoin, Tokyo, New York, 1981. When the protein is secreted out of the tumor cell, the protein in a medium can be quantified without extracting the protein from the tumor cell.

When the protein level or levels of the gene or genes listed in Table 3 increase, or the protein level or levels of the gene or genes listed in Table 4 decrease, it is determined that the tumor cells are susceptible to the anticancer agent.

The present invention also provides an immunoassay reagent for use in the test method of the present invention, which comprises an antibody directed to the protein as a component. The antibody used as a component can be obtained as described above. The immunoassay reagent of the present invention may contain components conventionally used in ordinary immunoassay reagents in addition to the aforementioned antibody.

EXAMPLES

Hereafter, the present invention will be described more specifically with reference to the following specific examples. However, the present invention is not limited to them.

Example 1

Culture of E7070-Susceptible and E7070-Resistant Strains and Extraction of RNA

All cells were cultured in RPMI-1640 medium supplemented with 10% of fetal bovine serum, 100 units/ml of penicillin and 100 μg/ml of streptomycin at 37° C. under 5% $CO_2$.

E7070, or ER-35748 or ER-68487 represented by the structural formula shown below was added to the media of an E7070-susceptible strain HCT116-C9 and an E7070-resistant strain HCT116-C9-C1 at a concentration of 8 μM and the cells were cultured. Then, cells were recovered after 0, 3, 6 and 12 hours. Further, the cells were also cultured for 12 hours without adding the drug and recovered.

ER-35748

ER-68487

Total RNA was extracted from these cells and subjected to the subsequent analyses. The RNA extracted from the cells cultured for 12 hours with the drug and the RNA from extracted the cells cultured for 12 hours without the drug were used for the gene expression analysis using a DNA microarray described in Example 2. HCT116-C9 was a substrain isolated from HCT116 derived from human colon cancer (American Type Culture Collection, Manassas, Va., U.S.A.), and HCT116-C9-C1 was an E7070-resistant substrain obtained by culturing this HCT116-C9 in the presence of E7070 with gradually increasing the E7070 concentration.

Similarly, E7070 was added to the media of an E7070-susceptible strain LX-1 and an E7070-resistant strain LX-1-E2 at a concentration of 8 μM and the cells were cultured. Cells were recovered after 0, 3, 6 and 12 hours. Total RNA was extracted from these cells and subjected to the subsequent analyses. LX-1 (Cancer Chemotherapy Center, Japan Foundation for Cancer Research, Tokyo, Japan) was a cell strain derived from human parvicellular lung cancer, and LX-1-E2 is an E7070-resistant substrain obtained by culturing this LX-1 in the presence of E7070 with gradually increasing the E7070 concentration.

Figure 1:
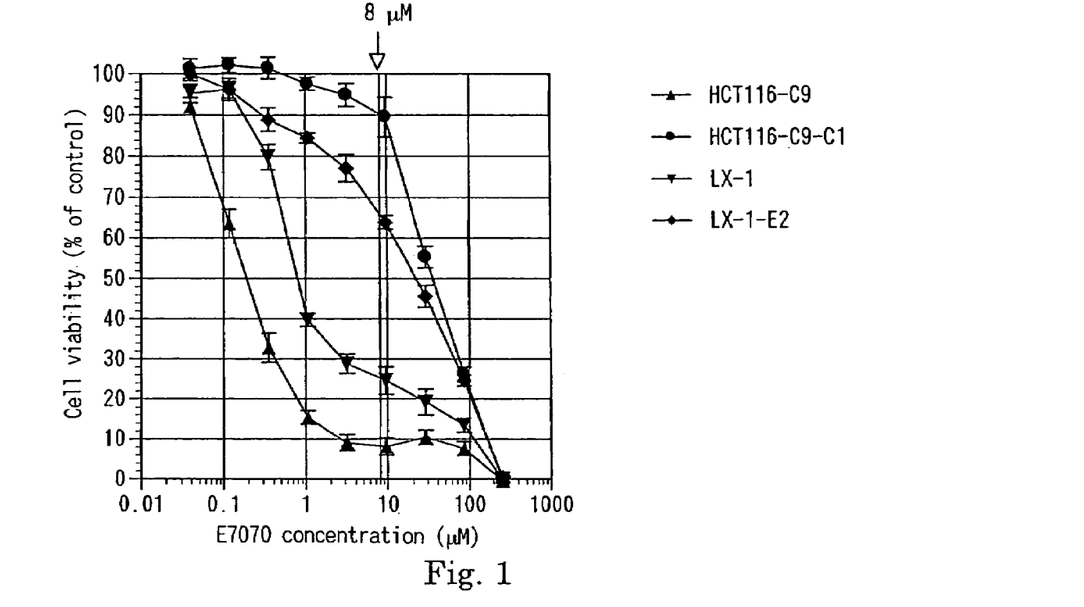
FIG. 1 shows cell growth inhibition curves obtained with E7070, of cell strains HCT116-C9, HCT116-C9-C1, LX-1 and LX-1-E2.
Figure 2:
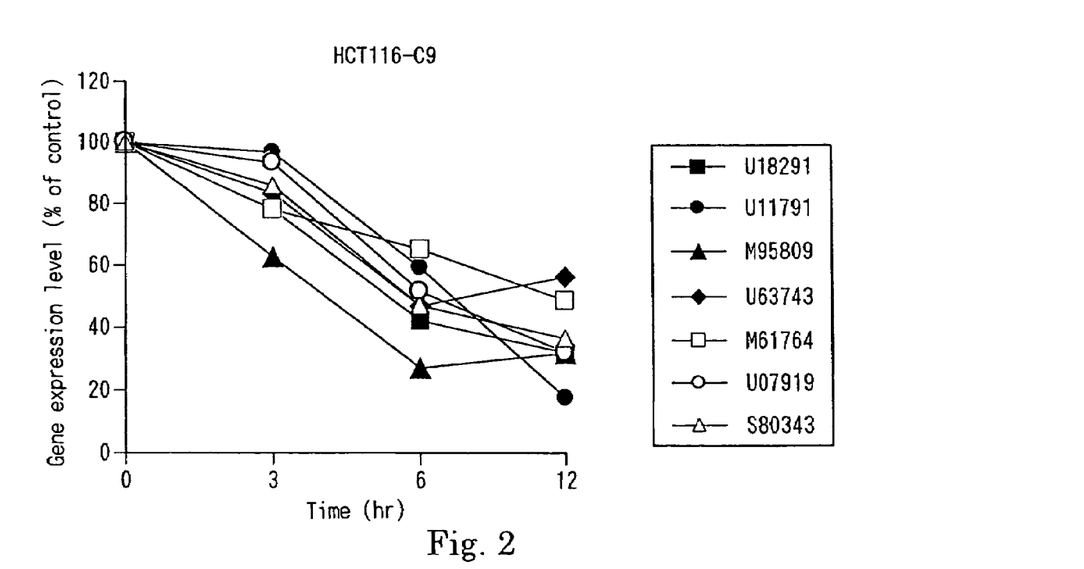
FIG. 2 shows results of analysis of variations in gene expression in the E7070-susceptible strain HCT116-C9 by quantitative PCR.

The used cell strains HCT116-C9, HCT116-C9-C1, LX-1 and LX-1-E2 were cultured for 72 hours with addition of E7070. Cell growth inhibition curves measured by the MTT method (Mosmann T., J. Immunol. Methods, 65, 55 (1983)) are shown in FIG. 1. The actual operation was performed by using CellTiter 96 Non-Radioactive Cell Proliferation Assay (Promega, Madison, Wis.) according to the attached operation manual.

Total RNA was extracted from the recovered cells by using TRIZOL Reagent (Life Technologies Oriental) according to the attached operation manual.

Example 2

Gene Expression Analysis Using DNA Microarray

1) Synthesis of cDNA and Biotinylated cRNA

Each RNA obtained in Example 1 was dissolved in 100 μl of sterilized water treated with diethyl pyrocarbonate (DEPC) and further purified by using RNeasy Column (QIAGEN), and double-stranded cDNA was synthesized by using SuperScript Choice System (Life Technologies Oriental) and a T7-d(T)$_{24}$ primer.

First, to 10 μg of RNA, 5 μM T7-d(T)$_{24}$ primer, 1×First strand buffer, 10 mM DTT, 500 μM dNTP mix and 20 units/μl of SuperScript II Reverse Transcriptase were added and the mixture was allowed to react at 42° C. for 1 hour to synthesize single-stranded DNA. Subsequently, to the DNA, 1×Second strand buffer, 200 μM dNTP mix, 67 U/ml of DNA ligase, 270 U/ml of DNA polymerase I and 13 U/ml of RNase H were added and the mixture was allowed to react at 16° C. for 2 hours to synthesize double-stranded cDNA. Further, to the cDNA, 67 U/ml of T4 DNA polymerase I was added and the mixture was allowed to react at 16° C. for 5 minutes and then 10 μl of 0.5 M EDTA was added to terminate the reaction.

The obtained cDNA was purified with phenol/chloroform, and a labeling reaction with biotinylated UTP and CTP was carried out by using RNA Transcript Labeling Kit (Enzo Diagnostics) according to the attached operation manual. The reaction product was purified with Rneasy Column and heated in 200 mM Tris/acetate buffer (pH 8.1), 150 mM magnesium acetate, 50 mM potassium acetate at 94° C. for 35 minutes to obtain fragment cRNA.

2) Hybridization with DNA Microarray (GeneChip) and Measurement

The fragmented cRNA was hybridized with GeneChip Hu6800 (Affymetrix) in 100 mM MES, 1 M sodium salt, 20 mM EDTA and 0.01% Tween 20 at 45° C. for 16 hours. After the hybridization, the GeneChip was washed and stained according to the protocol EukGE-WS2 attached to Affymetrix Fluidics Station. For the staining, streptavidin-phycoerythrin and biotinylated goat anti-streptavidin antibody were used. The stained GeneChip was scanned by using HP Argon Ion Laser Confocal Scanner (Hewlett Packard) to measure its fluorescence intensity. The fluorescence was measured at 570 nm by using an excitation light at 488 nm.

The quantitative data analyses were all conducted by using GeneChip Software (Affymetrix). To quantify RNA, an average of "differences [(Perfect match hybridization signal)−(Mismatch signal)]" was obtained for each probe family. When this value was 50 or higher, and quantitative values of RNA measured under two kinds of conditions diverge, preferably they diverge 1.8 times or more, it was determined that the gene expression had significantly "increased" or "decreased".

E7070, or ER-35748 or ER-68487 was added to a medium for HCT116-C9 at a concentration of 8 µM and culture was performed. The results of analysis of RNA extracted from the cells at 12 hours by using GeneChip were compared with the results of RNA analysis for HCT116-C9 cells obtained in the same manner except for not adding the drug. As a result, a list of genes of which expression levels were increased in common by the treatments with three types of drugs, E7070, ER-35748 and ER-68487 (GenBank registration numbers are also shown (the same shall apply in other tables shown below)) is shown in Table 1. Similarly, a list of genes of which expression levels were decreased in common by the treatments with the three types of drugs is shown in Table 2.

TABLE 1

| Registration number | Gene name |
| --- | --- |
| D59253 | NCBP interacting protein 1 |
| D78514 | Ubiquitin-conjugating enzyme |
| D83767 | Rep-8 |
| HG1139-HT4910 | FK506-Binding protein |
| HG3484-HT3678 | Cdc-like kinase 1 (Clk1) |
| J04152 | Tumor-associated antigen GA733-1, M1S1 |
| M21154 | S-adenosylmethionine decarboxylase |
| M60724 | p70 Ribosomal S6 kinase alpha-1 |
| M84349 | Transmembrane protein CD59 |
| S61953 | c-ErbB3 receptor tyrosine kinase |
| U52960 | RNA polymerase II complex component SRB7 |
| U84720 | Export protein RAE1 |
| U92014 | Defective mariner transposon Hsmar2 |
| Z18951 | Caveolin |

TABLE 2

| Registration number | Gene name |
| --- | --- |
| AB000409 | Serine/threonine protein kinase MNK1 |
| AB000450 | Putative serine/threonine protein kinase VRK2 |
| AB002380 | Leukemia-associated Rho GEF |
| AB003102 | Proteasome 26S subunit p44.5 |
| AC002045 | CIT987SK-A-589H1 |
| AF002020 | Niemann-Pick C disease protein (NPC1) |
| AF008445 | Phospholipid scramblase |
| D00723 | Hydrogen carrier protein, glycine synthase |
| D14659 | KIAA0103 |
| D21852 | KIAA0029 |

TABLE 2-continued

| Registration number | Gene name |
| --- | --- |
| D26535 | Dihydrolipoamide succinyltransferase |
| D28364 | Annexin II |
| D29677 | KIAA0054 |
| D29810 | Unknown product |
| D29956 | Ubiquitin specific protease 8 |
| D30756 | KIAA0049 |
| D31883 | Actin-binding LIM protein |
| D32002 | Nuclear cap binding protein |
| D38521 | KIAA0077 |
| D38552 | KIAA0073 |
| D38553 | KIAA0074 |
| D43947 | KIAA0100 |
| D43948 | ch-TOG |
| D50645 | SDF2 |
| D50663 | Dynein (TCTEL1) |
| D50912 | RNA-binding motif protein 10 |
| D50916 | Ubiquitination factor E4A |
| D61391 | PAP39 |
| D63480 | KIAA0146 |
| D63506 | Syntaxin-binding protein 3 |
| D63875 | TPR-containing/SH2-binding protein |
| D63880 | KIAA0159 |
| D78586 | Multifunctional protein CAD |
| D79983 | KIAA0161 |
| D79987 | KIAA0165 |
| D79988 | KIAA0166 |
| D79991 | KIAA0169 |
| D83776 | KIAA0191 |
| D83781 | KIAA0197 |
| D84307 | Phosphoethanolamine cytidylyltransferase |
| D86981 | Amyloid precursor protein-binding protein 2 |
| D87435 | KIAA0248 |
| D87446 | KIAA0257 |
| D87448 | DNA topoisomerase II-binding protein |
| D87743 | Solute carrier family 9 |
| HG1869-HT1904 | Male enhanced antigen |
| HG2379-HT3996 | Serine hydroxymethyltransferase, cytosolic |
| HG4094-HT4364 | Transcription factor Lsf-Id |
| J04088 | DNA topoisomerase II (top2) |
| J04501 | Muscle glycogen synthase |
| J04543 | Synexin |
| L06845 | Cysteinyl-tRNA synthetase |
| L07033 | Hydroxymethylglutaryl-CoA lyase |
| L07540 | Replication factor C, 36-kDa subunit |
| L07597 | Ribosomal protein S6 kinase 2 |
| L07758 | IEF SSP 9502 |
| L21936 | Succinate dehydrogenase flavoprotein subunit |
| L25444 | TAFII70-alpha |
| L25931 | Lamin B receptor |
| L33075 | Ras GTPase-activating-like protein IQGAP1 |
| L33881 | Protein kinase C iota isoform |
| L38810 | Proteasome 26S subunit p45 |
| L40395 | Eukaryotic initiation factor 2B-beta |
| L41870 | Retinoblastoma susceptibility protein (RB1) |
| L47276 | Alpha topoisomerase truncated-form |
| M15796 | PCNA |
| M19267 | Tropomyosin |
| M22632 | Mitochondrial aspartate aminotransferase |
| M23379 | GTPase-activating protein ras p21 |
| M24486 | Prolyl 4-hydroxylase alpha subunit |
| M29204 | DNA-binding factor |
| M29550 | Calcineurin A1 |
| M30496 | Ubiquitin carboxyl-terminal hydrolase |
| M33518 | HLA-B-associated transcript 2 (BAT2) |
| M34309 | Epidermal growth factor receptor HER3 |
| M37400 | Cytosolic aspartate aminotransferase |
| M55905 | Mitochondrial NAD(P) + dependent malic enzyme |
| M58525 | Catechol-O-methyltransferase |
| M59911 | Integrin alpha-3 |
| M61764 | Gamma-tubulin |
| M62994 | Filamin B |
| M74089 | TB1 |
| M85085 | Cleavage stimulation factor |
| M86707 | Myristoyl CoA: protein N-myristoyl transferase |
| M87338 | Replication factor C, 40-kDa subunit (A1) |
| M87339 | Replication factor C, 37-kDa subunit (RFC4) |

TABLE 2-continued

| Registration number | Gene name |
|---|---|
| M88163 | Global transcription activator (hSNF2/SWI2) |
| M91432 | Medium-chain acyl-CoA dehydrogenase (MCAD) |
| M92439 | Leucine-rich protein |
| M93056 | Monocyte/neutrophil elastase inhibitor |
| M95809 | Basic transcription factor 62 kD subunit (BTF2) |
| M95929 | Homeobox protein PHOX1 |
| M97935 | Transcription factor ISGF-3 |
| S58544 | 75 kDa infertility-related sperm protein |
| S59184 | RYK = related to receptor tyrosine kinase |
| S72904 | APK1 antigen = MAb KI recognized |
| S78085 | PDCD2, Rp8 homolog |
| S80343 | Arginyl-tRNA synthetase (ArgRS) |
| U01062 | Inositol 1,4,5-triphosphate receptor type 3 |
| U02566 | Receptor tyrosine kinase tif |
| U04285 | Lysosomal acid lipase |
| U06631 | H326 |
| U07231 | G-rich sequence factor-1 |
| U07681 | Isocitrate dehydrogenase 3 (NAD+) alpha |
| U07919 | Aldehyde dehydrogenase 6 (ALDH6) |
| U08815 | Splicesomal protein SAP61 |
| U10324 | Nuclear factor NF90 |
| U11791 | Cyclin H |
| U15174 | Nip3 |
| U15306 | DNA-binding protein NFX1 |
| U18291 | CDC16Hs |
| U18934 | Receptor tyrosine kinase DTK |
| U20979 | Chromatin assembly factor-I p150 subunit |
| U22233 | Methylthioadenosine phosphorylase |
| U23028 | Eukaryotic initiation factor 2B-epsilon |
| U23946 | LUCA15 |
| U26648 | Syntaxin 5A |
| U27459 | Origin recognition complex protein 2 homolog |
| U27460 | Uridine diphosphoglucose pyrophosphorylase |
| U28413 | Cockayne syndrome complementation group A |
| U28811 | Cystein-rich fibroblast growth factor receptor |
| U28831 | Immuno-reactive with anti-PTH Ab |
| U28963 | Gps2 |
| U30313 | Diadenosine tetraphosphatase |
| U30521 | P311 HUM −3.1 |
| U30827 | Splicing factor SRp40-3 (SRp40) |
| U30828 | Splicing factor SRp55-2 (SRp55) |
| U34252 | Gamma-aminobutyraldehyde dehydrogenase |
| U34683 | Glutathione synthetase |
| U36341 | SLC6A8 |
| U40282 | Integrin-linked kinase |
| U46006 | Smooth muscle LIM protein (h-SmLIM) |
| U49844 | FRAP-related protein (FRP1/ATR) |
| U50078 | Guanine nucleotide exchange factor p532 |
| U50939 | Amyloid precursor protein-binding protein 1 |
| U53468 | NADH: ubiquinone oxidoreductase subunit B13 |
| U57629 | Retinitis pigmentosa GTPase regulator |
| U60808 | CDP-diacylglycerol synthase |
| U61145 | Enhancer of zeste homolog 2 |
| U61263 | Acetolactate synthase homolog |
| U63743 | Mitotic centromere-associated kinesin (MCAK) |
| U65785 | Oxygen-regulated protein ORP150 |
| U72514 | C2f |
| U72515 | C3f |
| U76764 | CD97 |
| U77413 | O-linked GlcNAc transferase |
| U77949 | Cdc6-related protein (HsCDC6) |
| U79241 | Clone 23759 |
| U80034 | Mitochondrial intermediate peptidase precursor |
| U81554 | CaM kinase II isoform |
| U85611 | DNA-PK interaction protein (KIP) |
| U89606 | Pyridoxal kinase |
| U90426 | Nuclear RNA helicase |
| U94319 | Transcription coactivator p75 (DFS70) |
| U95740 | 362G6.1 |
| U97188 | Putative RNA binding protein KOC |
| X06745 | DNA polymerase alpha subunit |
| X13482 | U2 snRNP-specific A protein |
| X51956 | Neuron specific (gamma) enolase |
| X53587 | Integrin beta-4 |
| X54199 | GARS-AIRS-GART |
| X54867 | NKG2-A |
| X59871 | T cell factor 1 |
| X61100 | 75 kDa subunit NADH dehydrogenase precursor |
| X66364 | Serine/threonine protein kinase PSSALRE |
| X68836 | S-adenosylmethionine synthetase |
| X70476 | Subunit of coatomer complex |
| X75535 | PxF |
| X81003 | HCG V |
| X84740 | DNA ligase III |
| X94754 | Yeast methionyl-tRNA synthetase homologue |
| X98248 | Sortilin |
| X99209 | Arginine methyltransferase |
| Y08612 | Nup88 |
| Y08682 | Carnitine palmitoyltransferase I type I |
| Y13115 | Serine/threonine protein kinase SAK |
| Z11518 | Histidyl-tRNA synthetase |
| Z17227 | Transmenbrane receptor protein CRF2-4 |
| Z46629 | SOX9 |
| Z68747 | Imogen 38 |

Two kinds of E7070-resistant strains (C9-C1 and another resistant strain (C9-C4) obtained in the same method as C9-C1) were treated with 8 µM of E7070 for 12 hours in the same manner as described above, and variations of the gene expression were analyzed by using GeneChip for the genes listed in Tables 1 and 2. As a result, no gene that increased or decreased 1.8 times or more was observed in the both strains.

From the above results, it is apparent that genes of which expression levels are changed in common by the treatments with these three types of anticancer agents can be used as surrogate markers of antitumor effect of E7070 and its related compounds by measuring each of their changes or changes of two or more of them in combination.

Example 3

Gene Expression Analysis by Quantitative PCR

In order to confirm that variations in gene expression obtained in Example 2 reflected the susceptibility of a tumor cell to E7070, changes of gene expression in E7070-susceptible cells and E7070-resistant cells were examined by quantitative PCR using RNA shown in Example 1, SYBR Green and ABI Prism 7700 Sequence Detection System (Perkin-Elmer Applied Biosystems).

The operation was performed in two steps of a reverse transcription reaction and PCR reaction. The reverse transcription reaction as the first step was carried out by adding 1×TaqMan RT buffer, 5.5 mM MgCl$_2$, 500 µM dNTP mix, 2.5 µM oligo d(T)$_{16}$ primer, 0.4 U/µl of RNase inhibitor and 1.25 U/µl of Multiscribe Reverse Transcriptase (Perkin-Elmer Applied Biosystems) to 1 µg of the total RNA, keeping the mixture at 25° C. for 10 minutes and then heating it at 48° C. for 30 minutes. The reaction was terminated by heating at 95° C. for 5 minutes.

The obtained cDNA was subjected to the PCR reaction as the second step. The PCR reaction was carried out in a reaction system composed of 4 ng of cDNA, 1×SYBR PCR buffer, 3 mM MgCl$_2$, 200 µM each of dATP, dCTP and dGTP, 400 µM dUTP, 200 nM primer pair, 0.01 U/µl AmpErase UNG and 0.025 U/µl AmpliTaq Gold DNA Polymerase (Perkin-Elmer Applied Biosystems). The PCR reaction was performed with reactions at 50° C. for 2 minutes and at 95° C. for 10 minutes followed by a cycle of reactions at 95° C. for 20 seconds, at 55° C. for 20 seconds and at 72° C. for 30 seconds, which are repeated 40 times. As the primers, oligonucleotides having the nucleotide sequences of SEQ ID NOS: 1 and 2 were used for GAPDH, those of SEQ ID NOS: 3 and 4 for S80343, those of SEQ ID NOS: 5 and 6 for U07919, those of SEQ ID NOS: 7 and 8 for U11791, those of SEQ ID NOS: 9 and 10 for M95809, those of SEQ ID NOS: 11 and 12 for U18291, those of SEQ ID NOS: 13 and 14 for U63743, and those of SEQ ID NOS: 15 and 16 for M61764.

Figure 3:
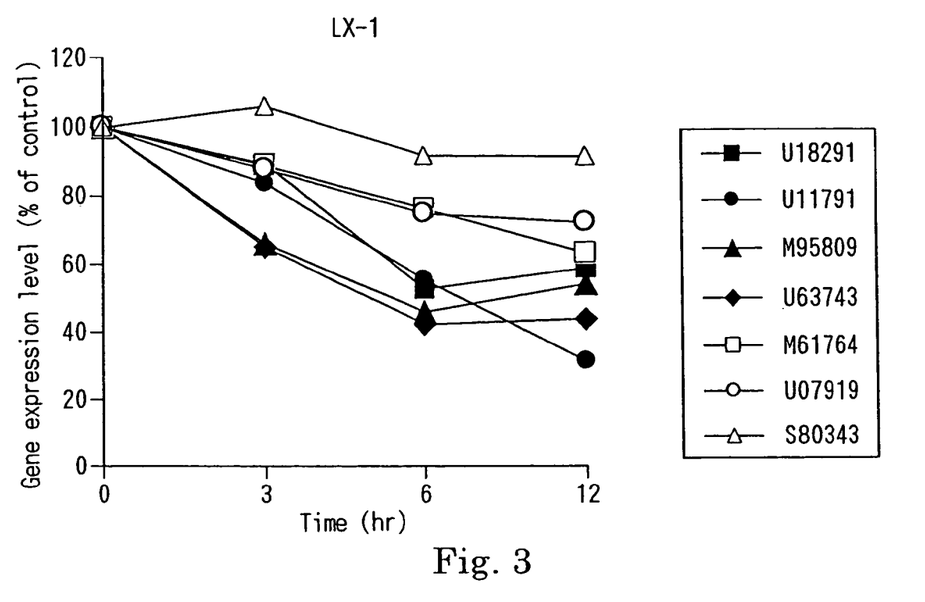
FIG. 3 shows results of analysis of variations in gene expression in the E7070-susceptible strain LX-1 by quantitative PCR.
Figure 4:
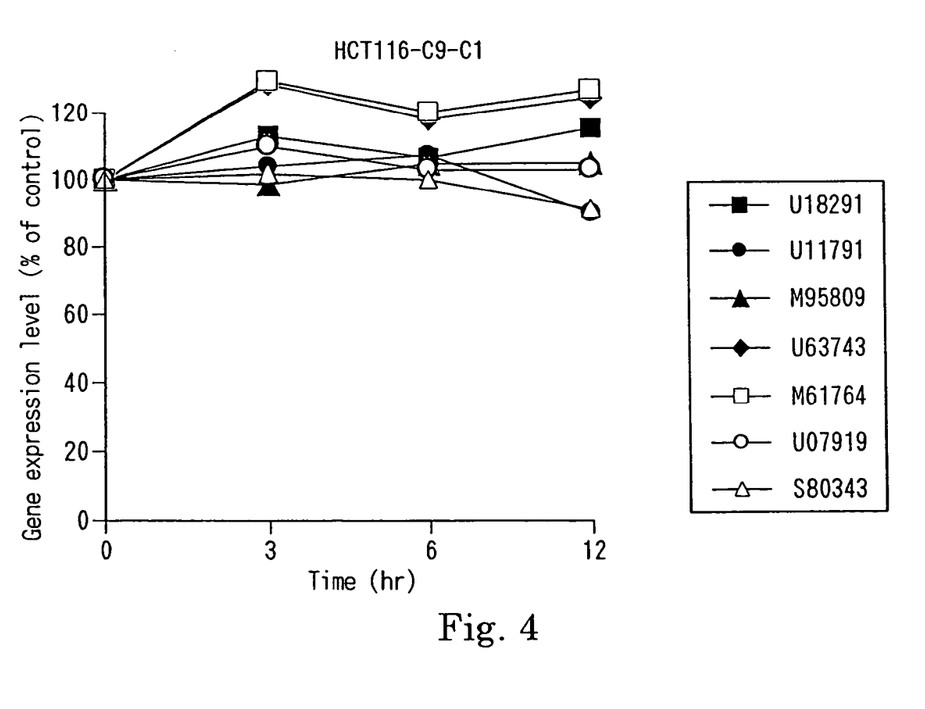
FIG. 4 shows results of analysis of variations in gene expression in the E7070-resistant strain HCT116-C9-C1 by quantitative PCR.
Figure 5:
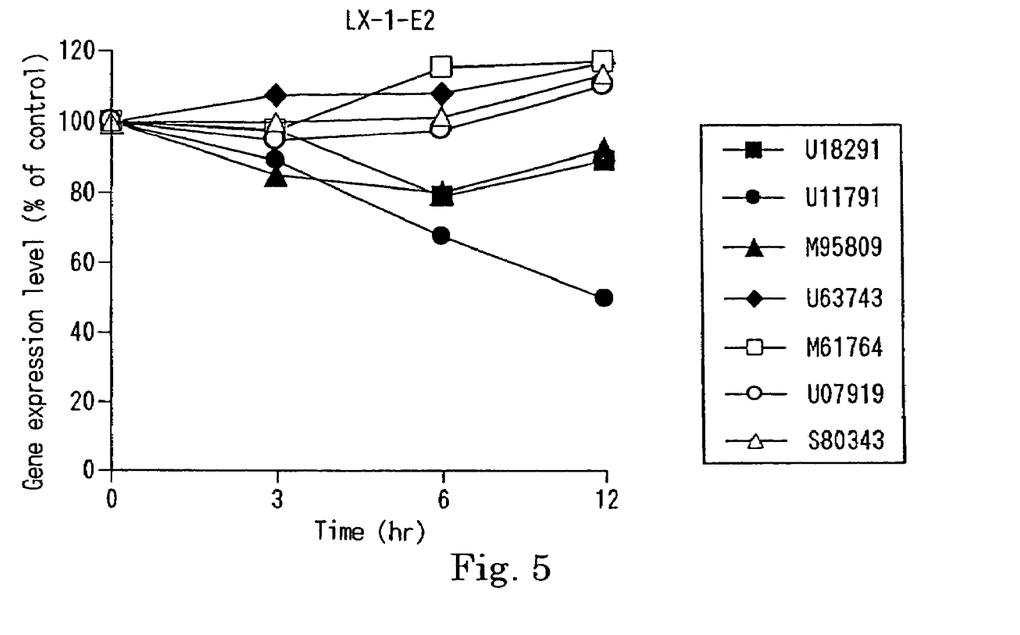
FIG. 5 shows results of analysis of variations in gene expression in the E7070-resistant strain LX-1-E2 by quantitative PCR.

The mRNA level in each specimen was quantified by measuring fluorescence intensity. In comparison of two or more specimens, quantitative values were corrected based on the mRNA level of GAPDH in each specimen. The relationships between the drug treatment time and each mRNA level are shown in FIGS. 2 to 5, where the quantified value at 0 hour after the drug treatment was used as a control (100%). The genes showed the largest expression variation in HCT116-C9 with the highest susceptibility (FIG. 2), and in the susceptible strain LX-1, all the genes except for S80343 showed expression variations although the variation magnitudes were smaller than those in HCT116-C9 (FIG. 3). On the other hand, no expression variation was observed for the resistant strain HCT116-C9-C1 (FIG. 4), and in the resistant strain LX-1-E2, which showed some growth inhibitory effect at the drug concentration of 8 µM used in the experiment, U11791 showed an expression change and M95809 and U18291 showed a slight expression change (FIG. 5).

The variations in expression of the gene retrieved in Example 2 correlated to the susceptibility to E7070, and it was confirmed that the genes retrieved in Example 2 could be used solely or in combination as surrogate markers of antitumor effect of E7070 and its related compounds.

Example 4

Analysis by ELISA

Among the genes listed in Table 2 in Example 2, the expression level of X51956 (Human ENO2 gene for neuron specific (gamma) enolase), which has been reported to be secreted out of the cell, was examined by the already reported ELISA method (Duncan M. E., McAleese S. M., Booth N. A., Melvin W. T., and Fothergill J. E., J. of Immunol. Methods, 151, 227-236, 1992, Yamaguchi K., Aoyagi K., Urakami K., Fukutani T., Maki N., Yamamoto S., Otsubo K., Miyake Y., and Kodama T., Jpn. J. Cancer Res., 86, 698-705, 1995). The actual measurement was carried out by using NSE ELISA Kit produced by Eiken Chemical (Tokyo) according to the attached reference.

Example 5

Gene Expression Analysis in Three Kinds Cancers

Gene expression changes in three kinds of cancers of HCT116-C9 (human colon cancer cell strain), MDA-MB-435 (human breast cancer cell strain) and MOLT-4 (human T lymphoblastic leukemia cell strain) caused by E7070 (treated with 8 µM for 12 hours) were examined by using GeneChip in the same manner as in Example 2.

A list of the genes of which expression was enhanced 1.8 times or more in common in the three kinds of cancers is shown in Table 3. Further, a list of the genes of which expression was inhibited 1.8 times or more in common in the three kinds of cancers is shown in Table 4. Since the genes of which expression varies (enhanced or reduced) in common in these strains of the three kinds of cancers established from cancer patients with totally different genetic backgrounds are very likely to be more closely associated with the E7070 antitumor action mechanism common to the tumor cells, it is considered that they can be used as valid markers when susceptibility of a tumor cell to E7070 and its related compounds is tested.

TABLE 3

| Registration number | Gene name |
|---|---|
| D78514 | Ubiquitin-conjugating enzyme |
| D83767 | Rep-8 |
| HG1139-HT4910 | Fk506-Binding protein |
| HG3484-HT3678 | Cdc-like kinase 1 (Clk1) |
| M21154 | S-adenosylmethionine decarboxylase |
| M60724 | p70 Ribosomal S6 kinase alpha-1 |
| S61953 | c-ErbB3 receptor tyrosine kinase |
| U52960 | RNA polymerase II complex component SRB7 |
| U84720 | Export protein RAE1 |
| U92014 | Defective mariner transposon Hsmar2 |

TABLE 4

| Registration number | Gene name |
|---|---|
| AB000409 | Serine/threonine protein kinase MNK1 |
| AB000450 | Putative serine/threonine protein kinase VRK2 |
| AC002045 | CIT987SK-A-589H1 |
| AF008445 | Phospholipid scramblase |
| D00723 | Hydrogen carrier protein, glycine synthase |
| D14659 | KIAA0103 |
| D21852 | KIAA0029 |
| D26535 | Dihydrolipoamide succinyltransferase |
| D32002 | Nuclear cap binding protein |
| D38521 | KIAA0077 |
| D38553 | KIAA0074 |
| D43947 | KIAA0100 |
| D50912 | RNA-binding motif protein 10 |
| D61391 | PAP39 |
| D63480 | KIAA0146 |
| D63880 | KIAA0159 |
| D78586 | Multifunctional protein CAD |
| D79983 | KIAA0161 |
| D79991 | KIAA0169 |
| D83781 | KIAA0197 |
| D84307 | Phosphoethanolamine cytidylyltransferase |
| D87446 | KIAA0257 |
| HG1869-HT1904 | Male enhanced antigen |
| HG2379-HT3996 | Serine hydroxymethyltransferase, cytosolic |
| HG4094-HT4364 | Transcription factor Lsf-Id |
| J04088 | DNA topoisomerase II (top2) |
| L07758 | IEF SSP 9502 |
| L21936 | Succinate dehydrogenase flavoprotein subunit |
| L25931 | Lamin B receptor |
| L38810 | Proteasome 26S subunit p45 |
| L41870 | Retinoblastoma susceptibility protein (RB1) |
| L47276 | Alpha topoisomerase truncated-form |
| M19267 | Tropomyosin |
| M22632 | Mitochondrial aspartate aminotransferase |
| M29204 | DNA-binding factor |
| M29550 | Calcineurin A1 |
| M30496 | Ubiquitin carboxyl-terminal hydrolase |
| M34309 | Epidermal growth factor receptor HER3 |
| M55905 | Mitochondrial NAD(P) + dependent malic enzyme |
| M61764 | Gamma-tubulin |
| M85085 | Cleavage stimulation factor |
| M87338 | Replication factor C, 40-kDa subunit (A1) |
| M91432 | Medium-chain acyl-CoA dehydrogenase (MCAD) |
| M92439 | Leucine-rich protein |
| M93056 | Monocyte/neutrophil elastase inhibitor |
| M95809 | Basic transcription factor 62 kD subunit (BTF2) |
| M97935 | Transcription factor ISGF-3 |
| S72904 | APK1 antigen = MAb KI recognized |
| S78085 | PDCD2, Rp8 homolog |
| U01062 | Inositol 1,4,5-triphosphate receptor type 3 |
| U07231 | G-rich sequence factor-1 |
| U08815 | Splicesomal protein SAP61 |
| U11791 | Cyclin H |
| U15306 | DNA-binding protein NFX1 |

TABLE 4-continued

| Registration number | Gene name |
|---|---|
| U18291 | CDC16Hs |
| U18934 | Receptor tyrosine kinase DTK |
| U20979 | Chromatin assembly factor-I p150 subunit |
| U22233 | Methylthioadenosine phosphorylase |
| U23028 | Eukaryotic initiation factor 2B-epsilon |
| U23946 | LUCA15 |
| U28831 | Immuno-reactive with anti-PTH Ab |
| U28963 | Gps2 |
| U30828 | Splicing factor SRp55-2 (SRp55) |
| U34683 | Glutathione synthetase |
| U40282 | Integrin-linked kinase |
| U49844 | FRAP-related protein (FRP1/ATR) |
| U50939 | Amyloid precursor protein-binding protein 1 |
| U57629 | Retinitis pigmentosa GTPase regulator |
| U61145 | Enhancer of zeste homolog 2 |
| U72514 | C2f |
| U77413 | O-linked GlcNAc transferase |
| U77949 | Cdc6-related protein (HsCDC6) |
| U79241 | Clone 23759 |
| U80034 | Mitochondrial intermediate peptidase precursor |
| U81554 | CaM kinase II isoform |
| U89606 | Pyridoxal kinase |
| U94319 | Transcription coactivator p75 (DFS70) |
| X06745 | DNA polymerase alpha subunit |
| X13482 | U2 snRKP-specific A protein |
| X51956 | Neuron specific (gamma) enolase |
| X54199 | GARS-AIRS-GART |
| X61100 | 75 kDa subunit NADH dehydrogenase precursor |
| X68836 | S-adenosylmethionine synthetase |
| X70476 | Subunit of coatomer complex |
| X75535 | PxF |
| X99209 | Arginine methyltransferase |
| Y08612 | Nup88 |
| Y08682 | Carnitine palmitoyltransferase I type I |
| Z17227 | Transmembrane receptor protein CRF2-4 |

INDUSTRIAL APPLICABILITY

According to the present invention, by measuring an expression level or levels of a gene or genes listed in Tables 3 and 4 in a tumor cell collected from a cancer patient treated with an anticancer agent represented by the general formula (I) or causing the anticancer agent represented by the general formula (I) to act on a tumor cell collected from a cancer patient and measuring an expression level or levels of a gene or genes listed in Tables 3 and 4, susceptibility of the tumor cell to the anticancer agent can be examined.

What is claimed is:

1. A method for testing susceptibility of a tumor cell to an anticancer agent, which comprises:

1) measuring an expression level or levels of a gene or genes selected from the group consisting of the genes glutathione synthetase (GenBank Accession No. U34683:

gggagaaccgttcgcggaggaaaggcgaactagtgttgggatggccacca actgggggagcctcttgcaggataaacagc agctagaggagctggcacggcaggccgtggaccgggccctg- gctgagggagtattgctgaggacctcacaggagcccacttcctcgga ggtggtgagctatgccccat- tcacgctcttcccctcactggtc- cccagtgccctgctggagcaagcctatgctgtgcagatggacttcaacct gctagtggatgctgtcagccagaacgct- gccttcctggagcaaactctttccag- caccatcaaacaggatgactttaccgctcgtctctttgac atccacaag- caagtcctaaaagagggcattgcccagactgtgttcctgggcctgaatcgc- tcagactacatgttccagcgcagcgcagatg gctccccagccctgaaaca- gatcgaaatcaacaccatctctgc- cagctttggggccctggcctcccggaccccagctgtgcaccgacatgt tctcagtgtcctgagtaagaccaaa- gaagctggcaagatcctctctaataatc- ccagcaagggactggccctgggaattgccaagcctgg gagctctacggctcacccaatgctctggtgctactgattgctcaagagaaggaaagaaaca- tatttgaccagcgtgccatagagaatgagct actgccaggaacatccat- gtgatccgacgaacatttgaa- gatatctctgaaaagggggtctctggaccaagaccgaaggctgtttgtggatg gccaggaaattgctgtggtttacttc- cgggatggctacatgcctcgtcagta- cagtctacagaattgggaagcacgtctactgctggagaggt cacatgct- gccaagtgcccagacattgccacccagctggctgggactaagaaggtgc- agcaggagctaagcaggccgggcatgctgga gatgttgctccctggc- cagcctgaggctgtggcccgcctc- cgcgccacctttgctggcctctactcactggatgtgggtgaagaaggggac caggccatcgccgaggcccttgctgc- ccctagccggtttgtgctaaagcccca- gagagagggtggaggtaacaacctatatggggagga aatggtacaggc- cctgaaacagctgaaggacagtgaggagagggcctcctacatcctcatg- gagaagatcgaacctgagccttttgagaa ttgcctgctacggcctg- gcagccctgcccgagtggtccagtg- catttcagagctgggcatctttggggtctatgtcaggcaggaaaagacac tcgtgatgaacaagcacgtggggcatc- tacttcgaaccaaagccatcgagcatg- cagatggtggtgtggcagcgggagtggcagtcctgg acaacccatac- cctgtgtgagggcacaaccaggccacgggaccttctatcctctgtatttgtc- attcctctcctagccctcctgaggggtatcc tcctaaagacctccaaagtttt- tatggaagggtaaatactggtaccttc- ccccagctttccatctgaggaccagaaaagttgtgtctcccttagat gagatctagacgcccccaaatcct- tgagatgtgggtatagctcaggg- taagctgctctgaggtaaaggtccatgaaccctgccccactcctg tcagc- ccctcatcagccttttcagcaggttcagtgcctgacttgggataggactga- gtggtaggaggagggggagtggaggggcatagc cttcccttaattctgc- cttaaataaaactgcattgctgt (SEQ ID NO: 17)), mitochondrial NAD(P)⁺ dependent malic enzyme (GenBank Accession No. M55905:

gctgagcatcgccagggcgggcg- gcagggcgcggcctctccgccgggtg- tacctcctgtcgcggcgcgagacctctggtgaaagaaaa gatgttgtc- ccggttaagagtagtttccaccacttgtactttggcatgtcgacatttgcaca- taaaagaaaaaggcaagccacttatgctgaacc caagaacaaacaagg- gaatggcatttacttacaagaacga- caaatgcttggtcttcaaggactctacctcccaaaatagagacacaagat attcaagcctacgatttcatagaaact- tgaagaaaatgactagcccttg- gaaaaatatatctacataatgggaatacaagaaagaaatgaga aattgttt- tatagaatactgcaagatgacattgagagtttaatgccaattgtatatacacc- gacggttggtcttgcctgctcccagtatggacaca tctttagaagac- ctaagggattatttatttcgatctcaga- cagaggtcatgttagatcaattgtg- gataactggccagaaaatcatgttaaggctg ttgtagtgactgatgggagagagaat- tctgggtcttggagatctgggtgtc- tatggaatgggaattccagtaggaaaactttgtttgtatacagctt gtgcag- gaatacggcctgatagatgcctgccagtgtgtattgatgtgggaactgataa- tatcgcactcttaaaagacccatttttacatgggctt gtaccagaaac- gagatcgcacacaacagtatgatgacct- gattgatgagtttatgaaagctattact- gacagatatggccggaacacactcat tcagttcgaagactttggaaatcataat- gcattcaggttcttgagaaagtac- cgagaaaaatattgtactttcaatgatgatattcaagggacag ctgcag- tagctctagcaggtcttcttgcagcacaaaaagttattagtaaaccaatctcc- gaacacaaaatcttattccttggagcaggagaggc tgctcttggaattg- caaatcttatagttatgtctatggta- gaaaatggcctgtcagaacaagaggca- caaaagaaaatctggatgtttgacaagt atggtttattagttaagggacggaaag- caaaaatagatagttatcaggaaccatt- tactcactcagccccagagagcataacctgatactttga agatgcagt- gaatatactgaagccttcaactattattggagttgcaggtgctggccgtctttt- cactcctgatgtaatcagagccatggcctctat caatgaaaggcctg- taatatttgcattaagtaatcctacag- cacaggcagagtgcacggctgaagaag- catatacacttacagagggcaggt gtttgtttgccagtggcagtc- catttgggccagtgaaacttaca- gatgggcgagtctttacaccaggtcaaggaaacaatgtttatattttccag gtgtggctttagctgttattctctgtaa- cacccggcatattagtgacagtgttttc- ctagaagctgcaaaggccctgacaagccaattgacagat gaa- gagctagcccaagggagactttacccaccgcttgctaatattcaggaagttt- ctattaacattgctattaaagttacagaatacctatatgct aataaaatg- gctttccgatacccagaacctgaaga- caaggccaaatatgttaaagaaagaa- catggcggagtgaatatgattccctgctgcc agatgtgtatgaatggccagaatctg- catcaagccctcctgtgataacagaata- gaagcactccctgataaatactttctgtgctccaggga accccttttttca- gacaagaagagataatgtcttcagtttt (SEQ ID NO: 18)), mitochondrial intermediate peptidase precursor (GenBank Accession No, U80034:

gcggagcgcgcgctcccagcgaaagcag- cagggcagggatctgcgttggaggaagg- gactgctctggtgctagaatgctgtgcgtcgg aaggctgggcggcttgg- gagccagagcagcagctctgccgccccgccgggcgggccggggaagc- ctcgaagccgggatccgggcc cgaaggggtcagcaccagctggtctc- ccgtgggcgccgccttcaatgtcaagc- cccagggcagccgcttggacctgttcggcgagcgggc gcgtcttttg- gagttcctgagctgagtgccccagaaggatttcatattgcacaagaaaaag- ccttgagaaagacagaattgcttgtgaccgt gcatgttccaccccac- ctgggccccagaccgtgctgatcttc- gatgagctctcggattccttatgcagagtggccgacttggctgattttgtga aaatcgctcaccctgagccagcattca- gagaagctgcggaagaagcttgtagaag- tattggcaccatggtgagaagttaacacaaatgt ggatttatat- caaagtttgcaaaaattactagctgataaaaaacttgtggattcccttgatcc- agaaacaaggcgagtggctgaactgttttatgtt tgattttgaaattagtg- gaatccatctagacaaacaaaagcg- taaaagagcagtggacctcaatgttaaaatcttggatttgagtagtacattct tatgggaaccaatttcccaacaagat- tgagaagcatctcttaccgaacacat- tcgtcgtaacttacatctgctggggatcatatcataattga tggtctccacg cagaatcaccagatgacttggtgcgagaagctgcttataaaattttttctttatc-
caatgctggtcaattgaaatgtttagaaga attgctcagcagcagagatct-
tctggcaaagttggtggggtattc-
cacgttttctcacagggctctccaaggaacgatagctaaaaatccaga
gactgtcatgcagttccttgaaaaac-
tatctgacaaactttctgaaagaactct-
gaaagattttgagatgatacgagggatgaaaatgaaactg aatgct-
caaaattccgaagtaatgccctgggaccccccttactacagtggtgtgattc-
gtgcagaaaggtataatattgagcccagcctatatt gcccgttttctctcttg-
gagcatgcatggaaggcct-
gaatattttgcttaacagactgttggg-
gatttcattatatgcagagcagcctgcaaaag
gagaggtgtggagcgaagatgtc-
cgaaaactggctgttgttcatgaatct-
gaaggattgttggggtacatttactgtgattttttttcagcgagca gacaaac-
cacatcaggattgccatttcactatccgtggaggcagactaaaggaagatg-
gagactatcaactcccacttgtagttcttatgctg aatcttccccgttcct-
caaggagttctccaactttgctaactc-
ctggcatgatggaaaatcttttccatgaaatgggacatgccatgcattcaatg
ctaggacgtactcgttaccaacacgt-
cactgggaccaggtgccctact-
gattttgctgaggttccttcttctctgatggagtactttgcaaatgat tatcgag-
tagttaaccaatttgccagacattatcagactggacagccactgccaaaaaa-
tatggtgtctcgtctttgtgaatctaaaaggttttgt gctgcagctgatatg-
caacttcaggtctttatgccactctg-
gatcaaatctaccatgggaagcatcccctgaggaattcaaccacagacattc
tcaaggaaacacaagagaaattctatg-
gcctaccatatgttccaaatactgcctg-
gcagctgcgattcagccacctcgtggggtatggtgcta gatattactcttac-
ctcatgtccagagcggtcgcctccatggttttggaaggagtgttttctacagg-
atcctttcaacagggctgccggggagcg ctatcgcagggagatgctggc-
ccacggtggaggcagggagcccatgct-
catggttgaaggtatgcttcagaagtgtccttctgttgatgact tcgtaagt-
gccctcgtttccgacttggatctggacttcgaaactttcctcatggattctgaa-
taaagaaacactctacacctctaatcaaggtca act tggaataaat
aatttgtttt aattaaaaaa aaaaaaaaaaa (SEQ ID NO: 19)),
and cyclin H (GenBank Accession No. U11791:
ggacgctgatgcgtttgggttctcgtct-
gcagaccctctggacctggtcacgattc-
cataatgtaccacaacagtagtcagaagcggcactg gaccttctccagc-
gaggagcagctggcaagactgcgggctgacgccaaccgcaaattcaga-
tgcaaagccgtggccaacgggaaggtt cttccgaatgatccagtcttct-
tgagcctcatgaagaaatgacactctg-
caaatactatgagaaaaggttattggaattctgttcggtgtttaag ccag-
caatgccaagatcgttgtgggtacggcttgtatgtatttcaaacgtttttatctt-
aataactcagtaatggaatatcaccccaggataataa tgctcacttgtg-
cattttggcctgcaaagtagatgaat-
tcaatgtatctagtcctcagtttgttg-
gaaacctccgggagagtcctcttggacagg
agaaggcacttgaacagatactg-
gaatatgaactacttcttatacag-
caacttaatttccaccttattgtccacaatccttacagaccatttgagg gcttc-
ctcatcgacttaaagacccgctatcccatattggagaatccagagattttga-
ggaaaacagctgatgacttcttaatagaattgcattga cggatgcttac-
ctttatacacaccttcccaaattgc-
cctgactgccattttatctagtgcctc-
cagggctggaattactatggaaagttatttatca
gagagtctgatgctgaaagagaaca-
gaacttgcctgtcacagttacta-
gatataatgaaaagcatgagaaacttagtaaagaagtatgaacc acccca-
gatctgaagaagttgctgttctgaaacagaagttggagcgatgtcattctgct-
gagcttgcacttaacgtaatcacgaagaagaggaa aggctatgaagat-
gatgattacgtctcaaagaaatccaaa-
catgaggaggaagaatggactgatgacgacctggtagaatctctctaaccat
ttgaagttgatttctcaatgctaac-
taatcaagagaagtaggaagcatat-
caaacgtttaactttatttaaaaagtataatgtgaaaacataaaata tattaaaactttctctattgttttctttcccttcacagtaactttatgtaaaataaaccat-
cttcaaaag (SEQ ID NO: 20)), in a tumor cell collected
from a cancer patient treated with an anticancer agent
represented by the following general formula (I):

wherein A represents benzene which may be substituted
with cyano or sulfonamido,
B represents benzene which may be substituted with
methyl, ethyl, n-propyl, or isopropyl,
C represents pyrrole which may be substituted with cyano
or a chlorine atom,
W represents a single bond,
X represents —NH—,
Y represents a carbon atom, and
Z represents —NH—, and
2) determining that the tumor cell is susceptible to the
anticancer agent when the expression level or levels of
the gene or genes decrease in comparison with those in
a tumor cell collected from the cancer patient before the
treatment with the anticancer agent.

2. A method for testing susceptibility of a tumor cell to an
anticancer agent, which compromises:
1) causing an anticancer agent to act on a tumor cell col-
lected from a cancer patient, said anticancer agent being
represented by the following general formula (I):

wherein A represents benzene which may be substituted
with cyano or sulfonamido,
B represents benzene which may be substituted with
methyl, ethyl, n-propyl, or isopropyl,
C represents pyrrole which may be substituted with cyano
or a chlorine atom,
W represents a single bond,
X represents —NH—,
Y represents a carbon atom, and
Z represents —NH—
2) measuring an expression level or levels of a gene or
genes selected from the group consisting of the genes
glutathione synthetase (GenBank Accession No.
U34683:
gggagaaccgttcgcggaggaaaggcgaactagtgttgggatggccacca
actggggagcctcttgcaggataaacagc agctagaggagctg-
gcacggcaggccgtggaccgggccctg-
gctgagggagtattgctgaggacctcacaggagcccacttcctcgga ggtggtgagctatgccccattcacgctcttccctcactggtcccagtgccctgctggagcaagcctatgctgtgcagatggacttcaacctgctagtggatgctgtcagccagaacgctgccttcctggagcaaactcttccagcaccatcaaacaggatgacttaccgctcgtctcttttgac atccacaagcaagtcctaaaagagggcattgcccagactgtgttcctgggcctgaatcgctcagactacatgttccagcgcagcgcagatg gctccccagccctgaaacagatcgaaatcaacaccatctctgccagcttttgggggcctggcctcccggaccccagctgtgcaccgacatgt tctcagtgtcctgagtaagaccaaagaagctggcaagatcctctctaataatcccagcaagggactggccctgggaattgccaaagcctgg gagctctacggctcacccaatgctctggtgctactgattgctcaagagaaggaaagaaacatatttgaccagcgtgccatagagaatgagct actggccaggaacatccatgtgatccgacgaacatttgaagatatctctgaaaaggggtctctggaccaagaccgaaggctgtttgtggatggccaggaaattgctgtggtttacttccgggatggctacatgcctcgtcagtacagtctacagaattgggaagcacgtctactgctggagaggt cacatgctgccaagtcccagacattgccacccagctggctgggactaagaaggtgcagcaggagctaagcaggccgggcatgctgga gatgttgctccctggccagcctgaggcgtggcccgcctccgcgccaccttgctggcctctactcactggatgtgggtgaagaaggggaccaggccatcgccgaggcccttgctgccctagccggtttgtgctaaagcccagagagaggggtggaggtaacaactctatatgggagga aatggtacaggcctgaaacagctgaaggacagtgaggagagggcctcctacatcctcatggagaagatcgaacctgagccttttgaaga ttgcctgctacggcctggcagccctgcccgagtggtccagtgcatttcagagctgggcatctttggggtctatgtcaggcaggaaaagacac tcgtgatgaacaagcacgtggggcatctacttcgaaccaaagccatcgagcatgcagatggtggtgtggcagcgggagtggcagtcctgg acaacccataccctgtgtgagggcacaaccaggccacgggacctttcatcctctgtatttgtcattcctcctccctagccctcctgaggggtatcctcctaaagacctccaaagtttttatgaagggtaaatactggtaccttccccagctttccatctgaggaccagaaaagttgtgtctcccttagatgagatctagacgccccaaatcctgagatgtgggtatagctcagggtaagctgctctgaggtaaaggtccatgaaccctgccccactcctg tcagccctcatcagccttttcagcaggttccagtgcctgacttgggataggactgagtggtaggaggaggggagtggaggggcatagc ctttcctaattctgccttaaataaaactgcattgctgt (SEQ ID NO: 17)), mitochondrial NAD(P)⁺dependent malic enzyme (GenBank Accession No. M55905:
gctgagcatcgccagggcggcggcaggggcgcggcctctccgccgggtgtacctcctgtcgcggcgcgagacctctggtgaaagaaaa gatgttgtcccggttaagagtagtttccaccacttgtactttggcatgtcgacatttgcacataaaagaaaaaggcaagccacttatgctgaacc caagaacaaacaagggaatggcatttactttacaagaacgacaaatgcttggtcttcaaggacttctacctcccaaaatagagacacaagat attcaagccttacgatttcatagaaactgaagaaaatgactagcccttggaaaaatatatctacataatgggaatacaagaagaaatgaga aattgtttt atagaatactgcaagatgacattgagagttaatgccaattgtatatacaccgacggttggtcttgcctgctcccagtatggacaca tctttagaagactaagggattatttattcgatctcagacagaggtcatgttagatcaattgtgataactggccagaaatcatgttaaggctg ttgtagtgactgatggagagagaattctgggtcttggagatctgggtctatggaatgggaattccagtaggaaaactttgtttgtatacagctt gtgcaggaatacgcctgatagatgcctgccagtgtgtattgatgtgggaactgaaatcgcactcttaaaagacccatttacatgggctt gtaccagaaacgagatcgcacacaacagtatgatgacctgattgatgagtttatgaaagctattactgacagatatggccggaacacactcat tcagttcgaagactttggaaatcataatgcattcaggttcttgagaaagtaccgagaaaaatattgtactttcaatgatgatattcaagggacag ctgcagtagctctagcaggtctcttcagcacaaaaagttagtaaaccaatctccgaacacaaaatcttattccttggagcaggagaggc tgctcttggaattgcaaatcttatagttatgtctatggtagaaaatggcctgtcagaacaagaggcacaaaagaaatctggatgtttgacaagt atggtttattagttaagggacggaaagcaaaaatagatagttatcaggaaccattactcactcagccccagagagcatacctgatactttga agatgcagtgaatatactgaagccttcaactattattggagttgcaggtgctggccgtcttttcactcctgatgtaatcagagccatggcctctat caatgaaaggcctgtaatatttgcattaagtaatcctacagcacaggcagagtgcacggctgaagaagcatatacacttacagagggcaggt gtttgtttgccagtggcagtcatttgggccagtgaaacttacagatgggcgagtctttacaccaggtcaaggaaacaatgtttatattttccag gtgtggctttagctgttattctctgtaacacccggcatattagtgacagtgttttcctagaagctgcaaggccctgacaagccaattgacagat gaa gagctagcccaagggagactttacccaccgcttgctaatattcaggaagtttctattaacattgctattaaagttacagaataccatatgct aataaaatgcttttccgatacccagaacctgaagacaaggccaaatatgttaaagaaagaacatggcggagtgaatatgattccctgctgcc agatgtgtatgaatggccagaatctgcatcaagccctcctgtgataacagaatagaagcactccctgataaatactttctgtgctccaggga acccctttttcagacaagaagagataatgtcttcagtttt (SEQ ID NO: 18)), mitochondrial intermediate peptidase precursor (GenBank Accession No, U80034:
gcggagcgcgcgctcccagcgaaagcagcagggcagggatctgcgttgaggaaggg actgctctggtgctagaatgctgtgcgtcgg aaggctgggcggcttggagccagagcagcagctctgccgccccgccgggcgggccggggaagcctcgaagccgggatccgggcc cgaaggggtcagcaccagctggtctccgtgggcgccgccttcaatgtcaagccccagggcagccgcttggacctgttcggcgagcgggc gcgtcttttggagttcctgagctgagtgccccagaaggatttcatattgcacaagaaaaagccttgagaaagacagaattgcttgtggaccgt gcatgttcaccccactgggccccagaccgtgctgatcttcgatgagctctcgattcctatgcagagtggccgacttggctgattttgtgaaatcgctcaccctgagccagcattcagagaagctgcggaagaagcttgtagaagtattggcaccatggtagagaagttgaacacaaatgt ggatttatcaaagtttgcaaaaattactagctgataaaaaacttgtggattcccttgatccagaaacaaggcgagtggctgaactgtttatgtt tgattttgaaattagtggaatccatctagacaaacaaagcgtaaaagagcagtggacctcaatgttaaaatcttggatttgagtagtacatttct tatgggaaccaattttcccaacaagattgagaagcatctcttaccagaacacatcgtcgtaactttacatctgctggggatcatatcataattga tggtctccacgcagaatcaccagatgacttggtgcgagaagctgcttataaaattttctttatcccaatgctggtcaattgaaatgtttagaaga attgctcagcagcagagatctctctggcaaagttggtggggtattccacgtttctcacagggctctccaaggaacgatagctaaaaatccaga gactgtcatgcagttccttgaaaaactatctgacaaacttttctgaaagaactctgaaagattttgagatgatacgagggatgaaaatgaaactg aatgctcaaaattccgaagtaatgccctgggaccccccttactacagtggtgtgattcgtgcagaaaggtataatattgagcccagctatatt gccgttttttctctcttggagcatgcatggaaggcctgaatattttgcttaacagactgttggg gatttcattatatgcagagcagcctgcaaaag gagaggtgtggagcgaagatgtc- cgaaaactggctgttgttcatgaatct- gaaggattgttggggtacatttactgtgattttttcagcgagca gacaaac- cacatcaggattgccatttcactatccgtggaggcagactaaaggaagatg- gagactatcaactcccacttgtagttcttatgctg aatcttccccgttcct- caaggagttctccaactttgctaactc- ctggcatgatggaaaatcttttccatgaaatgggacatgccatgcattcaatg ctaggacgtactcgttaccaacacgt- cactgggaccaggtgccctact- gattttgctgaggttccttctattctgatggagtactttgcaaatgat tatcgag- tagttaaccaatttgccagacattatcagactggacagccactgccaaaaa- atatggtgtctcgtctttgtgaatctaaaaaggtttgt gctgcagctgatatgcaacttcag- gtcttttatgccactctggatcaaatc- taccatgggaagcatcccctgaggaattcaaccacagacattc tcaag- gaaacacaagagaaattctatggcctaccatatgttccaaatactgcctggc- agctgcgattcagccacctcgtggggtatggtgcta gatattactcttacct- catgtccagagcggtcgcctccatg- gtttggaaggagtgttttctacaggatc- ctttcaacagggctgccggggagcg ctatcgcagggagatgctggcccacg- gtggaggcagggagcccatgctcatggt- tgaaggtatgcttcagaagtgtccttctgttgatgact tcgtaagtgc- cctcgtttccgacttggatctggacttcgaaacttttcctcatggattctgaata- aagaaacactctacacctctaatcaaggtca act tggaataaat aatttgtttt aattaaaaaa aaaaaaaaaaaa (SEQ ID NO: 19)), and cyclin H (GenBank Accession No. U11791:

ggacgctgatgcgtttgggttctcgtct- gcagaccctctggacctggtcacgattc- cataatgtaccacaacagtagtcagaagcggcactg gaccttctccagc- gaggagcagctggcaagactgcgggctgacgccaaccgcaaattcagat- gcaaagccgtggccaacgggaaggtt cttccgaatgatccagtctttct- tgagcctcatgaagaaatgacactctg- caaatactatgagaaaaggttattggaattctgttcggtgtttaag ccag- caatgccaagatctgttgtgggtacggcttgtatgtatttcaaacgtttttatctt- aataactcagtaatggaatatcaccccaggataataa tgctcacttgtg- cattttggcctgcaaagtagatgaat- tcaatgtatctagtcctcagtttgttg- gaaacctccgggagagtcctcttggacagg agaaggcacttgaacagatactg- gaatatgaactacttcttatacag- caacttaatttccaccttattgtccacaatccttacagaccatttgagg gcttc- ctcatcgacttaaagacccgctatcccatattggagaatccagagattttga- ggaaaacagctgatgactttcttaatagaattgcattga cggatgcttac- cttttatacacaccttcccaaattgc- cctgactgccatttttatctagtgcctc- cagggctggaattactatggaaagttatttatca gagagtctgatgctgaaagagaaca- gaacttgcctgtcacagttacta- gatataatgaaaagcatgagaaacttagtaaagaagtatgaacc acccagatctgaagaagttgctgttctgaaacagaagttggagcgatgtcattctgct- gagcttgcacttaacgtaatcacgaagaagaggaa aggctatgaagatgatgattacgtctcaaagaaatccaaa- catgaggaggaagaatggactgatgacgacctggtagaatctctctaaccat ttgaagttgatttctcaatgctaac- taatcaagagaagtaggaagcatat- caaacgtttaactttatttaaaaagtataatgtgaaaacataaaata tat- taaaacttttctattgttttctttccctttcacagtaactttatgtaaaataaaccat- cttcaaaag (SEQ ID NO: 20)), in the tumor cell, and 3) determining that the tumor cell is susceptible to the anticancer agent the expression level or levels of the gene or genes decrease in comparison with those in an untreated tumor cell.

3. The method according to claim 1, wherein the expression level or levels of gene or genes are measured by quantifying an RNA or RNAs which are a transcription product or products of the gene or genes by using a DNA microarray.

4. The method according to claim 1, wherein the expression level or levels of the gene or genes are measured by quantifying an RNA or RNAs which are a transcription product or products of the gene or genes by quantitative PCR.

5. The method according to claim 2, wherein the expression level or levels of gene or genes are measured by quantifying an RNA or RNAs which are a transcription product or products of the gene or genes by using a DNA microarray.

6. The method according to claim 2, wherein the expression level or levels of the gene or genes are measured by quantifying an RNA or RNAs which are a transcription product or products of the gene or genes by quantitative PCR.

7. The method according to claim 1, wherein said anticancer agent is N-(3-chloro-7-indolyl)-1,4-benzenedisulfonamide.

8. The method according to claim 2, wherein said anticancer agent is N-(3-chloro-7-indolyl)-1,4-benzenesulfonamide.

* * * * *

SEQUENCE LISTING

```
<160> NUMBER OF SEQ ID NOS: 16

<210> SEQ ID NO 1
<211> LENGTH: 19
<212> TYPE: DNA
<213> ORGANISM: Artificial Sequence
<220> FEATURE:
<223> OTHER INFORMATION: primer

<400> SEQUENCE: 1
gaaggtgaag gtcggagtc                                                  19

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
gaagatggtg atgggatttc                                                 20

<210> SEQ ID NO 3
<211> LENGTH: 22
<212> TYPE: DNA
<213> ORGANISM: Artificial Sequence
<220> FEATURE:
<223> OTHER INFORMATION: primer

<400> SEQUENCE: 3
gcattttacg gttccctgag at                                              22

<210> SEQ ID NO 4
<211> LENGTH: 22
<212> TYPE: DNA
<213> ORGANISM: Artificial Sequence
```

```
<220> FEATURE:
<223> OTHER INFORMATION: primer

<400> SEQUENCE: 4
gatacgccac atgttcacct tc                                          22

<210> SEQ ID NO 5
<211> LENGTH: 24
<212> TYPE: DNA
<213> ORGANISM: Artificial Sequence
<220> FEATURE:
<223> OTHER INFORMATION: primer

<400> SEQUENCE: 5
cagaatcaat agcccagaga gctt                                        24

<210> SEQ ID NO 6
<211> LENGTH: 24
<212> TYPE: DNA
<213> ORGANISM: Artificial Sequence
<220> FEATURE:
<223> OTHER INFORMATION: primer

<400> SEQUENCE: 6
gttgtggcgt tagaagattg gatc                                        24

<210> SEQ ID NO 7
<211> LENGTH: 24
<212> TYPE: DNA
<213> ORGANISM: Artificial Sequence
<220> FEATURE:
<223> OTHER INFORMATION: primer

<400> SEQUENCE: 7
gtcattctgc tgagcttgca ctta                                        24

<210> SEQ ID NO 8
<211> LENGTH: 25
<212> TYPE: DNA
<213> ORGANISM: Artificial Sequence
<220> FEATURE:
<223> OTHER INFORMATION: primer

<400> SEQUENCE: 8
gagagattct accaggtcgt catca                                       25

<210> SEQ ID NO 9
<211> LENGTH: 23
<212> TYPE: DNA
<213> ORGANISM: Artificial Sequence
<220> FEATURE:
<223> OTHER INFORMATION: primer

<400> SEQUENCE: 9
ccaagttacg aagctctgtc cat                                         23

<210> SEQ ID NO 10
<211> LENGTH: 23
<212> TYPE: DNA
<213> ORGANISM: Artificial Sequence
<220> FEATURE:
<223> OTHER INFORMATION: primer

<400> SEQUENCE: 10
tgtaggctgt ctggagcatc tct                                         23
```

```
<210> SEQ ID NO 11
<211> LENGTH: 22
<212> TYPE: DNA
<213> ORGANISM: Artificial Sequence
<220> FEATURE:
<223> OTHER INFORMATION: primer

<400> SEQUENCE: 11
tgttgattcc tcagaacgca tc                                            22

<210> SEQ ID NO 12
<211> LENGTH: 24
<212> TYPE: DNA
<213> ORGANISM: Artificial Sequence
<220> FEATURE:
<223> OTHER INFORMATION: primer

<400> SEQUENCE: 12
tgtatcatct cgcctaagac caag                                          24

<210> SEQ ID NO 13
<211> LENGTH: 22
<212> TYPE: DNA
<213> ORGANISM: Artificial Sequence
<220> FEATURE:
<223> OTHER INFORMATION: primer

<400> SEQUENCE: 13
atctcaccag gcataagctc ct                                            22

<210> SEQ ID NO 14
<211> LENGTH: 23
<212> TYPE: DNA
<213> ORGANISM: Artificial Sequence
<220> FEATURE:
<223> OTHER INFORMATION: primer

<400> SEQUENCE: 14
acagttcctc ctcttccttg gat                                           23

<210> SEQ ID NO 15
<211> LENGTH: 21
<212> TYPE: DNA
<213> ORGANISM: Artificial Sequence
<220> FEATURE:
<223> OTHER INFORMATION: primer

<400> SEQUENCE: 15
ctcaagaggc tgacgcagaa t                                             21

<210> SEQ ID NO 16
<211> LENGTH: 23
<212> TYPE: DNA
<213> ORGANISM: Artificial Sequence
<220> FEATURE:
<223> OTHER INFORMATION: primer

<400> SEQUENCE: 16
ctggctgaca tgatggtaga cac                                           23
```